United States Patent
Pierce et al.

(10) Patent No.: US 8,980,327 B2
(45) Date of Patent: *Mar. 17, 2015

(54) CAPSULE AND POWDER FORMULATIONS CONTAINING LANTHANUM COMPOUNDS

(71) Applicant: Shire LLC, Florence, KY (US)

(72) Inventors: David Pierce, Hertfordshire (GB); Josephine Christine Ferdinando, Tadley (GB); Peter Neil Davies, Basingstoke (GB)

(73) Assignee: Shire LLC, Florence, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/507,439

(22) Filed: Oct. 6, 2014

(65) Prior Publication Data

US 2015/0024013 A1    Jan. 22, 2015

Related U.S. Application Data

(63) Continuation of application No. 14/193,543, filed on Feb. 28, 2014, which is a continuation of application No. 13/307,718, filed on Nov. 30, 2011, now Pat. No. 8,697,132, which is a continuation-in-part of application No. 12/958,380, filed on Dec. 1, 2010, now Pat. No. 8,263,119.

(51) Int. Cl.
*A61K 9/48* (2006.01)
*A61K 33/24* (2006.01)
*A61K 9/14* (2006.01)
*A61K 47/36* (2006.01)
*A61K 47/02* (2006.01)

(52) U.S. Cl.
CPC . *A61K 9/14* (2013.01); *A61K 33/24* (2013.01); *A61K 47/36* (2013.01); *A61K 47/02* (2013.01)
USPC ........................ 424/489; 424/617; 424/715

(58) Field of Classification Search
None
See application file for complete search history.

(56) References Cited

U.S. PATENT DOCUMENTS

| 4,428,927 A | 1/1984 | Ebert et al. |
| 5,030,447 A | 7/1991 | Joshi et al. |
| 5,968,976 A | 10/1999 | Murrer et al. |
| 7,381,428 B2 | 6/2008 | Ferdinando et al. |
| 7,465,465 B2 | 12/2008 | Haslam et al. |
| 7,618,656 B2 | 11/2009 | Hallenbeck et al. |
| 2005/0079135 A1* | 4/2005 | Haslam et al. ............... 424/9.3 |
| 2006/0121127 A1 | 6/2006 | Ferdinando et al. |
| 2006/0153932 A1 | 7/2006 | Ferdinando et al. |
| 2007/0259052 A1 | 11/2007 | Hallenbeck et al. |
| 2008/0187602 A1 | 8/2008 | Ferdinando et al. |
| 2009/0017133 A1 | 1/2009 | Haslam et al. |

FOREIGN PATENT DOCUMENTS

| EP | 1785141 A1 | 5/2007 |
| WO | WO-2010085520 A1 | 7/2010 |
| WO | WO-2010106557 A2 | 9/2010 |

OTHER PUBLICATIONS

Capsugel, Coni-Snap Capsules, Reliable and Consistent Two-Piece Capsules, brochure, Feb. 2008.
Stegemann and Bornem, Hard Gelatin Capsules Today—and Tomorrow,Capsugel Library, 2nd Edition, 2002.
Tousey, The Granulation Process 101: Basic Technologies for Tablet Making, Pharmaceutical Technology: Tableting & Granulation 2002, pp. 8-13.
International Search Report and Written Opinion for International Patent Application No. PCT/US2011/062716 mailed Feb. 1, 2012.
Official Communication for U.S. Appl. No. 12/958,380 mailed Jan. 24, 2012.
Official Communication for U.S. Appl. No. 13/307,718 mailed Jun. 19, 2013.

* cited by examiner

*Primary Examiner* — Ernst V Arnold
(74) *Attorney, Agent, or Firm* — Frommer Lawrence & Haug LLP; Russell A. Garman

(57) ABSTRACT

The present invention includes an oral pharmaceutical capsule comprising a shell, lanthanum carbonate or lanthanum carbonate hydrate, and a lubricant such as talc, wherein the shell encapsulates the lanthanum carbonate or its hydrate and the lubricant. Capsule shells comprise, for example, gelatin. The present invention also includes an oral pharmaceutical powder comprising lanthanum carbonate or lanthanum carbonate hydrate and a pharmaceutically acceptable excipient. The oral pharmaceutical capsules and powders of the present invention can be administered to treat a patient at risk of or suffering from hyperphosphatemia, at risk of or suffering from chronic kidney disease (CKD), at risk of or suffering from soft tissue calcification associated with CKD, or at risk of or suffering from secondary hyperparathyroidism.

3 Claims, 11 Drawing Sheets

FIG 5 different lubricants without further ingredients (60°C for 1 weeks)

CAPSULE AND POWDER FORMULATIONS CONTAINING LANTHANUM COMPOUNDS

This application is a continuation of U.S. application Ser. No. 14/193,543 filed Feb. 28, 2014, which is a continuation of U.S. application Ser. No. 13/307,718, filed Nov. 30, 2011 and granted as U.S. Pat. No. 8,697,132, which is a continuation-in-part of U.S. application Ser. No. 12/958,380, filed Dec. 1, 2010 and granted as U.S. Pat. No. 8,263,119. Each of the above-referenced patents/applications is incorporated herein by reference.

FIELD OF THE INVENTION

The present invention includes an oral pharmaceutical capsule comprising a gelatin shell that encapsulates both lanthanum carbonate or lanthanum carbonate hydrate and a lubricant such as talc. The capsules of the present invention dissolve at a similar rate before and after storage. The present invention also includes oral pharmaceutical powders comprising lanthanum carbonate or lanthanum carbonate hydrate and pharmaceutically acceptable excipients. The powders of the present invention possess similar pharmacokinetic properties compared to lanthanum carbonate chewable tablets. The oral pharmaceutical capsules and powders of the present invention can be administered to treat a patient at risk of or suffering from hyperphosphatemia, at risk of or suffering from chronic kidney disease (CKD), at risk of or suffering from soft tissue calcification associated with CKD, or at risk of or suffering from secondary hyperparathyroidism.

BACKGROUND OF THE INVENTION

Hyperphosphatemia is a particular problem of patients with chronic renal insufficiency or chronic kidney disease (CKD). Approximately 70% of patients with end stage renal disease (ESRD) on renal dialysis therapy require treatment for hyperphosphatemia. This condition can lead to severe bone problems and metastatic calcification of skin and major organs and is associated with significant morbidity and mortality. Conventional dialysis fails to reduce the levels of phosphate in the blood, so that levels rise in time. Elevated phosphate levels are treated using a combination of dietary restrictions and phosphate binding agents. Chronic renal insufficiency patients also suffer from secondary hyperparathyroidism.

Certain forms of lanthanum carbonate have been used to treat hyperphosphatemia in patients with renal failure (see, e.g., JP 1876384). U.S. Pat. No. 5,968,976, owned by the assignee of the present invention, describes the preparation and use in a pharmaceutical composition of certain hydrates of lanthanum carbonate for the treatment of hyperphosphatemia. U.S. Pat. Nos. 7,381,428 and 7,465,465, also both owned by the assignee of the present invention, disclose formulations containing lanthanum carbonate and lanthanum carbonate hydrate.

The non-calcium, non-resin phosphate binder lanthanum carbonate as a chewable tablet (FOSRENOL®, Shire Pharmaceuticals, Basingstoke, UK) is commonly used in clinical practice for the reduction of serum phosphorus in patients with CKD Stage 5 who are undergoing dialysis. For patients who have trouble chewing lanthanum carbonate tablets, who find chewable tablets unpalatable, or who find chewing tablets several times per day tiresome, there is a need in the art for alternative formulations containing lanthanum carbonate or lanthanum carbonate hydrate.

SUMMARY OF THE INVENTION

The present invention includes an oral pharmaceutical capsule comprising a shell that encapsulates both lanthanum carbonate or lanthanum carbonate hydrate and a lubricant such as talc. The shell of the capsule includes, for example, gelatin. The capsules of the present invention dissolve at a similar rate before and after storage. Capsules can include additional encapsulated excipients such as diluents, disintegrants, and flow aids.

The present invention also includes oral pharmaceutical powders comprising lanthanum carbonate or lanthanum carbonate hydrate and pharmaceutically acceptable excipients. The powders of the present invention possess similar pharmacokinetic properties to those of lanthanum carbonate chewable tablets. Powders can include encapsulated excipients such as diluents, disintegrants, lubricants, and flow aids.

The oral pharmaceutical capsules and powders of the present invention can be administered to treat a patient at risk of or suffering from hyperphosphatemia. Further uses of the pharmaceutical capsules and powders include treating a patient (1) at risk of or suffering from chronic kidney disease (CKD), (2) at risk of or suffering from soft tissue calcification associated with chronic kidney disease (CKD), or (3) at risk of or suffering from secondary hyperparathyroidism by administering the capsules and powders of the invention to the patient.

BRIEF DESCRIPTION OF THE DRAWINGS

FIG. 5 is a graph comparing the dissolution profiles before and after storage at 60° C. for 1 week for the following formulations: (1) a formulation containing PEG 6000, (2) a formulation containing L-leucine, (3) a formulation containing L-leucine/PEG 6000, and (4) a formulation containing talc.

DETAILED DESCRIPTION OF THE INVENTION

Figure 1:
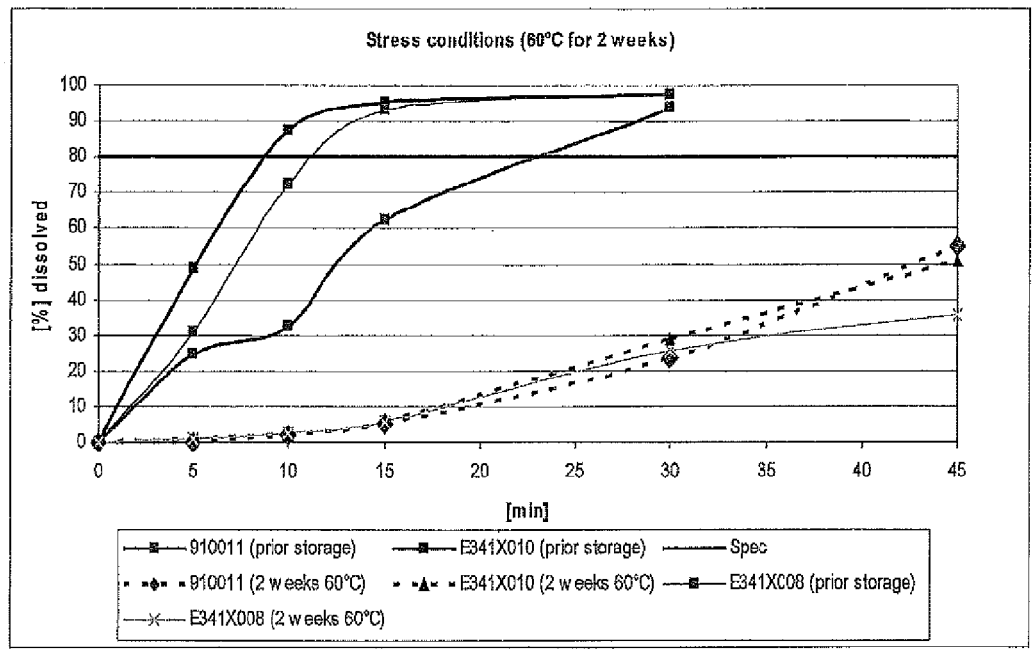
FIG. 1 is a graph comparing the dissolution rates of 3 lanthanum carbonate capsules (E341x008, E341X010, and 910011) before and after storage for 2 weeks at 60° C.

Capsule and powder formulations provide palatable alternatives to chewable tablets. Like chewable tablets, capsules and powders can be administered without liquid which is advantageous for patients with kidney disease who must regulate their liquid intake. Capsules can be chewed like a tablet or, for patients who have difficulty chewing, capsules can be opened and the contents can be sprinkled onto the tongue or onto food. Alternatively, capsules can be swallowed whole. Powders can also be sprinkled onto the tongue or onto food; they do not have to be chewed and are easy to swallow.

The present invention is based on the unexpected finding that the dissolution rate of lanthanum carbonate in oral pharmaceutical capsules, where the shell encapsulates both lanthanum carbonate hydrate and talc, are unaffected by storage while other encapsulated lubricants cause a reduction in the dissolution rate of lanthanum carbonate in capsules, as demonstrated in the Examples. A consistent dissolution rate before and after storage is necessary for regulatory approval, provides a consistent rate and extent of phosphate binding, and allows for greater shelf-life.

The present invention is also based on the unexpected finding that lanthanum carbonate powder formulations containing dextrates, colloidal silicon dioxide, crospovidone, and talc were both pharmacodynamically and pharmacokinetically equivalent to lanthanum carbonate tablet formulations. Without being bound to any particular theory, this result is contrary to the hypothesis that a powder formulation may result in more lanthanum in the blood plasma, compared to a lanthanum carbonate chewable tablet, because the powder may contain more finely ground particles which have a greater surface area, potentially, leading to faster dissolution and absorption.

In contrast to the lanthanum carbonate powder formulations described above and consistent with the above hypothesis, lanthanum carbonate powder formulations containing dextrates, colloidal silicon dioxide, and magnesium stearate were pharmacodynamically equivalent to lanthanum carbonate tablet formulations, but displayed 30% more lanthanum in the blood plasma compared to tablets. While this increase raises technical issues which make regulatory approval more difficult, the heightened amount of lanthanum in the plasma is still within between-study variation for the chewable tablet and not considered clinically significant.

Oral Pharmaceutical Powders

Oral pharmaceutical powders include an active ingredient such as lanthanum carbonate or lanthanum carbonate hydrate and one or more pharmaceutically acceptable excipients such as disintegrants, lubricants, diluents, flow aids, or combinations thereof.

The method of making oral powders generally includes optionally sieving the ingredients, mixing the ingredients, optionally slugging or roller compacting followed by milling to produce a coarse powder, and optionally sieving the coarse powder.

For example, lanthanum carbonate hydrate, dextrates, and colloidal silicon dioxide are sieved into a tumble blender and blended. Crospovidone and talc are sieved into the tumble blender and blended with the other ingredients. The blended powder is then passed through a roller compactor and the compacted material is passed through a sieve to mill the material into a free flowing powder.

The powders can then be filled into sachets, stick packs, or rigid containers such as glass or plastic bottles or vials either as unit doses or as bulk quantities from which individual doses can be measured with a suitable measuring device using methods known to one of ordinary skill in the art. Each sachet or stick pack can contain from about 200 mg to about 2000 mg of elemental lanthanum as lanthanum carbonate. For example, each sachet can contain 250 mg, 500 mg, 750 mg or 1000 mg of elemental lanthanum as lanthanum carbonate.

Oral Pharmaceutical Capsules

Oral pharmaceutical capsules include a shell that encapsulates an active ingredient such as lanthanum carbonate or lanthanum carbonate hydrate, and other optional ingredients such as a lubricant. The encapsulated material can be a powder as described above.

A capsule shell can be a hard gel. Hard gel capsule shells typically have a body and a cap. The body and cap materials can comprise a gelling agent and water. The gelling agent can be, but is not limited to, gelatin, modified starch, carrageenan, gellan, mannan gum, amylose, xanthan, alginates, agar, guar, gum arabic, pectin, cyclodextrin or a combination thereof. The shell can optionally include a gelling salt, a plasticizer, an emulsifier, thickener, preservative, flavoring, sweetener, pigment, radiation blocker, opacifying agent, anti-oxidant, masticatory substance, etc.

Gelatin can be manufactured by the partial hydrolysis of collagen from animal by-products such as bones, skin, and connective tissue. Bovine and porcine animals are the primary sources of gelatin.

Modified starches, include, for example, non-retrograding starches derived by chemical modification of starch from any plant source such as corn, waxy maize, potato, wheat, rice, tapioca, sorghum, etc. Useful modified starches are ether and ester derivatives of starch including, for example, hydroxypropyl, hydroxyethyl, succinate, and octenyl succinate starch derivatives. Other modified starches which may be used include the thermally converted, fluidity or thin boiling type products derived from the above chemically modified starches. These materials may be of lower molecular weight, prepared by heating the modified starch, subjecting the starch to hydrolytic acid and/or heat treatment, etc.

Carrageenan is a natural sulfated polysaccharide hydrocolloid derived from seaweed, and is a mixture of galactose and 3-6-anhydrogalactose copolymers. A number of different carrageenan types exist (e.g., kappa, iota, lambda, etc.) and it is anticipated that any of these may be used in the present invention.

Gellan gum is an extracellular polysaccharide obtained by aerobic fermentation of the microorganism, *Pseudomonas elodea*. Various forms of gellum gum including, but not limited to, native, deacetylated, deacylated clarified, partially deacetylated, partially deacylated clarified may be used in the present invention.

Mannam gum includes the galactomannan gums, the glucomannan gums and mixtures thereof. Accordingly, mannam gum includes, but is not limited to, locust bean gum, konjac gum, tara gum and *cassia* gum.

A gelling salt may be used in the present invention. Accordingly, a calcium salt, a magnesium salt, a barium salt, a sodium salt or a potassium salt of an appropriate inorganic or organic acid may be used to form the shell of a capsule of the present invention.

Plasticizers can also be added to the shell of a capsule formulation. Plasticizers can be polyols, for example, glycerin, sorbitol, an alkylene glycol, maltitol, lactitol, xylitol, corn syrup solids, etc. or a combination thereof.

Pigments can include indigotine (i.e., FD & C Blue 2), erythrosin (i.e., FD & C Red 3), and titanium dioxide, which also acts as an opacifer.

The body and cap of the capsule shell can comprise between about 10 wt % and 95 wt % gelling agent (e.g., gelatin), between about 75 wt % to about 95 wt % gelling agent, or between about 80 wt % and 90 wt % gelling agent of the weight of the shell. The body and cap of the capsule shell can comprise between about 5 wt % and 40 wt % water, between about 5 wt % and about 25 wt % water, or between about 10 wt % and 20 wt % water based on the total weight of the shell. The body and cap of the capsule shell can comprise up to about 10 wt % pigment, between about 0.1 wt % and about 2.5 wt % pigment, or between about 1.5 wt % and 2.5 wt % pigment of the weight of the shell.

Capsule shells can be purchased for example from Capsugel® (Peapack, N.J.) and Shionogi Qualicaps® (Whitsett, N.C.). Shells that can be used to encapsulate lanthanum carbonate formulations can be, for example, Capsugel® Coni-Snap® size 00 for 500 mg capsules and Capsugel® Coni-Snap® 0el (0 elongated) for 375 mg capsules, where the masses are based on the mass of elemental lanthanum in the lanthanum carbonate. The capsule can be tubular in shape and from about 0.4 inches to about 1.1 inches in closed length and from about 0.18 to about 0.4 inches in diameter with a volume of about 0.1 to about 1.4 mL. Briefly, capsule shells are made by dipping rods having dimensions of the cap and body of the capsule into a melted, pigmented gelatin solution, allowing the cap and body to solidify while rotating the rods to distribute the gelatin evenly, removing the cap and body from the rods, and fitting the cap and body with each other.

Several methods of producing capsules containing a powder are known in the art. A powder can be made as discussed in the section describing oral pharmaceutical powders above. The powder is then placed into one half of the capsule and the other half of the capsule shell is pressed onto the first half. See Stegemann and Bornem, "Hard gelatin capsules today—and tomorrow," $2^{nd}$ Edition 2002 from the Capsugel® Library and Tousey, "The Granulation Process 101: Basic Technologies for Tablet Making," *Pharmaceutical Technology Tableting & Granulation* 2002, pages 8-13.

A capsule can be tested for its stability during storage by storing the capsule under accelerated aging conditions and testing the capsule for its ability to dissolve before and after storage. Accelerated aging conditions include 25° C., 30° C., 40° C., 50° C., 60° C., 70° C., or 80° C. for 1, 2, 3, or 4 weeks or a month optionally at 55%, 60%, 65%, 70%, 75%, or 80% relative humidity (RH). These conditions can be correlated with room temperature conditions using the Arrhenius equation which relates rate of reaction (in this case, degradation/instability) to temperature. Conditions can also be internationally recognized standard conditions such as 25° C./60% RH, 25° C./65% RH, 30° C./60% RH, 30° C./65% RH, 30° C./75% RH, or 40° C./75% RH, 45° C./75% RH for 1, 2, 3, or 4 weeks or a month. Capsules before and after storage can be compared by testing their ability to dissolve in solution over time. For example as discussed in the Examples, capsules can be exposed to a 0.25 M HCl solution and the amount of dissolved lanthanum carbonate or lanthanum carbonate hydrate can be measured over time by titrating the lanthanum in solution with EDTA. The capsules of the present invention can be at least 60%, 70%, 80%, 90%, or 100% dissolved (based on, e.g., the amount of dissolved lanthanum) after 10, 20, 30, 45, or 60 minutes in a solution (e.g., 0.25 M HCl) after the capsules have been exposed to accelerated aging conditions. For example, the capsules of the present invention can be at least 80% dissolved (based on the amount of dissolved lanthanum) after 30 minutes in 0.25 M HCl after storage at 50° C. or 60° C. for 1 or 2 weeks.

Lanthanum Carbonate and Lanthanum Carbonate Hydrate

"Lanthanum carbonate" as used herein encompasses all hydrated forms of lanthanum carbonate as well as anhydrous lanthanum carbonate.

The capsule and powder formulations of the invention can contain lanthanum carbonate having the general formula $La_2(CO_3)_3 \cdot xH_2O$, wherein x has a value from 0 to 10. Preferably, x has a value from 3 to 8, desirably from 3 to 6. Most preferably, x may have an average value of about between 4 and 5. The hydration level of the lanthanum compound can be measured by methods well known in the art, such as x-ray powder diffraction (XRPD).

The amount of lanthanum carbonate in the powder or encapsulated in the shell of the capsule ranges from about 50 wt % to about 95 wt %, preferably from about 75 wt % to about 90 wt %, and most preferably from about 85 wt % to about 90 wt % based on the total weight of the powder or the contents of the capsule. In one embodiment, the amount of lanthanum carbonate in the powder or encapsulated in the shell of the capsule is about 87 wt % based on the total weight of the powder or the contents of the capsule.

The amount of elemental lanthanum as lanthanum carbonate in the powder or encapsulated in the shell of the capsule ranges from about 26 wt % to about 50 wt %, preferably from about 35 wt % to about 50 wt % and most preferably from about 40 wt % to about 50 wt % based on the total weight of the powder or the contents of the capsule. In one embodiment, the amount of elemental lanthanum as lanthanum carbonate in the powder or encapsulated in the shell of the capsule is about 45 wt % based on the total weight of the powder or the contents of the capsule.

The amount of elemental lanthanum in a sachet containing the lanthanum carbonate powder or in the lanthanum carbonate capsule can be 250 mg, 350 mg, 500 mg, 750 mg, or 1000 mg and preferably 250 mg, 350 mg, or 500 mg.

Additional Ingredients for Encapsulation or for Oral Pharmaceutical Powders

Additional ingredients (i.e., pharmaceutically acceptable excipients) that can be used for oral powders or encapsulated by the shell of a capsule include diluents, lubricants, flow aids, binders, disintegrants, colors, flavors, antioxidant, and sweeteners. The additional ingredients should be suitable for oral administration to renally impaired subjects.

A diluent can be added to the formulation in an amount from about 5 wt % to about 50 wt % based on the total weight of the powder or contents of the capsule. The total diluent amount can be from about 5 wt % to about 30 wt %, preferably from about 5 wt % to about 20 wt %, and most desirably from about 5 wt % to about 10 wt % based on the total weight of the powder or capsule contents of the formulation.

Diluents include a monosaccharide, a disaccharide, calcium sulfate dihydrate, an oligosaccharide, isomaltooligosaccharide, erythritol, polydextrose, dextrins, starch, maltodextrin, calcium lactate trihydrate, microcrystalline cellulose (such as Avicel™ available from GFS Chemicals (Powell, Ohio)), hydrolyzed cereal solids (such as Maltrons or Mor-Rex™), amylose, or glycine. One or more diluents can be present in the formulation.

Suitable monosaccharides for use in the formulation of the present invention include, but are not limited to, glyceraldehyde, erythrose, threose, ribose, lyxose, xylose, arabinose, allose, talsoe, gulose, mannose, glucose (e.g., in the form of corn syrup), idose, galactose, altrose, dihydroxyacetone, erythrulose, ribulose, xyloketose, psicose, tagatose, sorbose, fructose, sorbitol, xylitol, inositol, erythritol, and mannitol in either the D- or L-configuration, including derivatives and analogs thereof. Monosaccharides for use in this invention can be either cyclic (in either alph- or beta-form) or acyclic and can be used in the invention as mixtures. Other suitable monosaccharides include dextrose (D-glucose such as Cerelose™ available from Fisher Scientific (Hampton, N.H.)).

Suitable disaccharides for use in the present invention include, but are not limited to, sucrose (for example, in the form of Di-Pac™ available from Domino Foods in Baltimore, Md., Sugartab™ available from JRS Pharma (Patterson, N.Y.), confectioner's sugar, or Nutab), lactose (including anhydrous lactose and lactose monohydrate), maltose, isomaltose, cellobiose, trehalose, maltitol (in the form of Lycasin™ available from Roquette (Lestrem, France)), isomalt, lactitol, mixtures, derivatives, and analogs thereof. Disaccharides of this invention also include any combination of two monosaccharides linked by a glycosidic bond. Disaccharides can be either homodisaccharides (i.e., consisting of 2 monosaccharides that are the same) or heterodisaccharides (i.e., consisting of 2 monosaccharides that are different). Furthermore, monosaccharides and disaccharides can be used in the same formulation.

Other suitable monosaccharides and disaccharides can be found in Remington: The Science and Practice of Pharmacy (20$^{th}$ Edition, A. R. Gennaro editor, Lippincott Baltimore, Md.: Williams and Wilkins, 2000) at pages 409-413; and in Biochemistry (2$^{nd}$ Edition, Voet and Voet, New York: John Wiley & Sons, Inc., 1995) at pages 251-276. Hydrolyzed starches containing mono- and/or disaccharides can also be used in the formulations of the invention.

Dextrates can also be used as a monosaccharide/disaccharide diluent. The term "dextrates" as used herein refers to a purified mixture of saccharides that is mostly dextrose (e.g., not less than about 93.0% and not more than about 99.0%, calculated on the dried basis) and that results from a controlled enzymatic hydrolysis of starch. Dextrates can be either anhydrous or hydrated. "Dextrates" can refer to dextrates as defined in the official monograph found in National Formulary 21 (printed by Webcom Limited in Toronto, Canada; 2003). Dextrates are available from JRS Pharma (Patterson, N.Y.) as Emdex™.

Useful lubricants can be chosen from, for example, magnesium stearate, talc, mineral oil (liquid paraffin), polyethylene glycol, silica, colloidal anhydrous silica, colloidal silicon dioxide, hydrogenated vegetable oil, glyceryl behenate, L-leucine, L-leucine/polyethylene glycol 6000, polyethylene glycol 6000 or glyceryl monostearate. Useful flow aids can be chosen from, for example, silica, colloidal anhydrous silica, or colloidal silicon dioxide. Generally, lubricants stop a formulation from sticking to the process equipment while flow aids enable the formulation to flow freely while being processed. One ingredient can be both a lubricant and a flow aid. One or more lubricants can be present in a formulation. One or more flow aids can be present in a formulation. In one embodiment, the lubricant can be talc and the flow aid can be colloidal silicon dioxide.

The lubricant amount can be from about 0.01% to about 0.05%, preferably from about 0.01% to about 0.04%, and most desirably from about 0.01% to about 0.03% by weight of the powder or the capsule contents of the formulation. The flow aid amount can be from about 0.1% to about 4%, preferably from about 0.1% to about 3%, and most desirably from about 0.1% to about 2% by weight of the powder or the capsule contents of the formulation.

Disintegrants can be chosen from crospovidone, croscarmellose sodium, starches such as sodium starch glycolate and pregelatinized corn starches, clays, celluloses such as purified cellulose, microcrystalline cellulose, methylcellulose, carboxymethylcellulose and sodium carboxymethylcellulose, alginates, and gums such as agar, guar, locust bean, karaya, pectin and tragacanth gums. One or more disintegrants can be present in a formulation. The total disintegrant amount can be from about 1.0 wt % to about 15 wt %, preferably from about 3 wt % to about 10 wt %, and most desirably from about 3 wt % to about 5 wt % by weight of the powder or the capsule contents of the formulation.

Combination Therapies

Lanthanum carbonate powders and capsules can be administered with vitamin D, a calcium source, vitamin K, or a combination thereof. These additional ingredients can be mixed with the lanthanum carbonate or administered separately.

Often, a subject suffering from hyperphosphatemia or the symptoms of CKD is vitamin D deficient. Levels of 25-hydroxy vitamin $D_2$ are low at values less than about 16 ng/mL and replacement treatment aims for levels of greater than or equal to about 16 ng/mL. Levels of 1,25-dihydroxy vitamin $D_2$ are low at values less than about 22 pg/mL and replacement treatment aims for levels of greater than about 22 pg/mL. Thus, it becomes desirable to produce and administer to a patient a formulation containing lanthanum carbonate and vitamin D or an analog of vitamin D or to administer to a patient a separate formulation containing lanthanum carbonate and a separate formulation containing vitamin D or an analog of vitamin D.

Examples of vitamin D sources which may be used include 1,25 dihydroxy-vitamin D, the active metabolite of vitamin D (calcitriol, rocalcitrol). Examples of suitable vitamin D analogs include doxercalciferol (Hectorol™, available from Genzyme, Cambridge, Mass.) and paricalcitol (Zemplar™, available from Abbott Laboratories, Abbott Park, Ill.) One or more vitamin D sources or vitamin D analogs can be present in a formulation.

When Vitamin D is administered in a separate dosage form, vitamin D can be administered once per day to a patient requiring treatment.

Hyperphosphatemic subjects or subjects having symptoms of CKD often suffer from hypocalcaemia (i.e., a blood calcium concentration below about 8.5 mg/dL). Hence, a formulation of the invention can include lanthanum carbonate and a calcium source.

Examples of forms of calcium include calcium carbonate (e.g., Tums™ available from GlaxoSmithKline, Uxbridge, UK), calcium acetate (e.g., PhosLo™ available from Fresenius, Waltham, Mass.), and $CaCl_2$. One or more calcium sources can be present in a formulation.

A calcium source can also be administered in a separate dosage form and, in some instances, concurrently with a dosage form of this invention. In a specific embodiment, 1-2 tablets containing calcium are given 1-3 times per day to a patient requiring treatment.

A subject suffering from hyperphosphatemia or the symptoms of CKD can be vitamin K deficient. In another embodiment of the present invention, the formulation of the invention, in combination with vitamin K, is administered to a subject suffering from hyperphosphatemia or the symptoms of CKD to alleviate vitamin K deficiency. Examples of vitamin K sources include vitamin K1 (phylloquinone), vitamin K2 (menaquinone), and vitamin K3 (menadione).

Vitamin K can be combined in the same formulation as the lanthanum formulation or can be given in a different formulation. In a specific embodiment, 2.5 to 25 mg of vitamin K1 are administered once per day to a subject requiring treatment.

Treatment Methods

Subjects susceptible to or suffering from hyperphosphatemia, at risk of chronic kidney disease (CKD), having stage one to five CKD, susceptible to or suffering from soft tissue calcification associated with CKD, susceptible to or suffering from secondary hyperparathyroidism, or susceptible to or suffering from other as yet undiscovered conditions requiring control of phosphate absorption, can be treated by administering a therapeutically effective amount of a lanthanum carbonate powder or capsule formulation of the present invention.

As used herein, the terms "treat," "treating," or "treatment" mean the prevention, reduction, amelioration, partial or complete alleviation, or cure of hyperphosphatemia, chronic kidney disease (CKD), severe bone problems, soft tissue calcification, secondary hyperparathyroidism, or other as yet undiscovered conditions requiring control of phosphate absorption.

Further, as used herein, the term "subject" refers to a mammal (e.g., any veterinary medicine patient such as a domesticated animal, such as a dog or cat), or a human patient.

A "pharmaceutically effective amount" or "therapeutically effective amount" as used herein is an amount or dose of lanthanum carbonate sufficient (i) to detectably decrease the serum phosphate levels of a subject or (ii) at a minimum, to keep the serum phosphate levels of a subject substantially constant.

The term "symptom(s)" of those at risk of or having hyperphosphatemia, CKD, soft tissue calcification associated with CKD, or secondary hyperparathyroidism may be any functional or structural abnormality experienced by a subject and indicating kidney dysfunction. Among other abnormalities, as an example, one or more of the following symptoms may indicate risk for or the presence of CKD: a serum creatinine concentration above the normal range for body weight and muscle mass, a blood phosphate level of above about 4.5 mg/dL, any detectable amount of blood from the kidneys in the urine, a protein to creatinine ratio of greater than 0.3 mg/mg, an albumin to creatinine ratio of greater than 30 mg/g, an intact parathyroid hormone (PTH) concentration in the blood of above about 150 pg/mL (second generation parathyroid hormone assay), or a glomerular filtration rate (GFR) of below about 90 mL/min/1.73 $m^2$.

Subjects susceptible to or suffering from hyperphosphatemia can be treated by administering a therapeutically effective amount of a lanthanum carbonate formulation of the invention. Hyperphosphatemia as used herein refers to a condition of a patient having blood phosphate levels of above about 4.5 mg/dL.

The National Kidney Foundation-Kidney Disease Outcomes Quality Initiative ("NKF-K/DOQI" or "K/DOQI," as referred to herein) has defined chronic kidney disease (CKD) as either (1) having kidney damage as defined by structural or functional abnormalities of the kidney for 3 months or longer with or without a decreased glomerular filtration rate (GFR) or (2) having a GFR of less than 60 mL/min/1.73 $m^2$ for 3 months or longer with or without kidney damage. Structural or functional abnormalities are manifested by symptoms such as either pathologic abnormalities or markers of kidney damage, including abnormalities identified in imaging studies or the composition of blood or urine.

Examples of markers of kidney damage include a plasma creatinine concentration of above the normal range for body weight and muscle mass, Additional markers of kidney damage can include hematuria (i.e., any detectable amount of blood from the kidneys in the urine), proteinuria (i.e., a protein to creatinine ratio of greater than 0.3 mg/mg), albuminuria (i.e., an albumin to creatinine ratio of greater than 30 mg/g), an intact parathyroid hormone (PTH) concentration in the blood above about 150 pg/mL (second generation parathyroid hormone assay), or blood phosphate levels of above about 4.5 mg/dL. One specific marker of kidney disease is a GFR rate below normal (i.e., a GFR below about 90 mL/min/1.73 $m^2$).

K/DOQI has published guidelines that define five different stages of CKD (Am J Kidney Dis. 2001, 37(suppl 1):S1-S238). The following table provides a description of each of the five stages of CKD and the GFR ranges for each of the stages.

TABLE 1

Five Stages of Chronic Kidney Disease (CKD)

| Stage | Description At risk | GFR (mL/min/1.73 $m^2$) 90-120 (with CKD symptoms) |
|---|---|---|
| 1 | Kidney damage with normal or elevated GFR | ≥90 |
| 2 | Kidney damage with mildly reduced GFR | 60-89 |
| 3 | Moderately reduced GFR | 30-59 |
| 4 | Severely reduced GFR | 15-29 |
| 5 | Kidney Failure (ESRD) | <15 (or dialysis) |

Hyperphosphatemia in CKD subjects has several secondary effects. When a subject suffers from hyperphosphatemia, excess serum phosphate can precipitate serum calcium causing widespread ectopic extraskeletal calcification. Unwanted calcium deposits can occur in cardiovascular tissue, resulting in an increased risk of cardiovascular complications that often lead to death. Additionally, increased serum phosphate indirectly decreases intestinal calcium absorption. These two mechanisms work concurrently to reduce serum calcium levels.

A reduction in serum calcium levels can contribute to an increase in the production of parathyroid hormone (PTR) with the development of secondary hyperparathyroidism. Furthermore, recent studies show that high phosphate levels can stimulate PTH production directly and lead to secondary hyperparathyroidism. Continual stimulation of PTH secretion induces hyperplasia of the parathyroid gland that eventually could lead to a parathyroidectomy becoming necessary.

It is believed that the method of the present invention involving the administration of a lanthanum carbonate powder or capsule formulation not only reduces plasma phosphate levels but ameliorates the effects of CKD in subjects susceptible to or having any of stages one to five CKD, including hyperphosphatemia, ectopic extraskeletal calcification, serum hypocalcemia, and secondary hyperparathyroidism. It should however, be understood that this invention is not limited to any particular biochemical or physiological mechanism.

A subject having a symptom or symptoms of chronic kidney disease (CKD) can be treated by administering to the subject a therapeutically effective amount of a lanthanum carbonate powder or capsule formulation of the present application. The subject treated may beat risk of CKD or have any of stages one to five CKD. Subjects at risk of CKD or who have any of stages one to five CKD who may be treated may have one or more of the following symptoms: a blood phosphate level of above about 4.5 mg/dL, a plasma creatinine concentration above the normal range for body weight and muscle mass, any detectable amount of blood from the kidneys in the urine, a protein to creatinine ratio of greater than 0.3 mg/mg, an albumin to creatinine ratio of greater than 30 mg/g, an intact parathyroid hormone concentration in the blood above about 150 pg/mL (second generation parathyroid hormone assay), an abnormal GFR, or combination thereof.

A subject having a symptom or symptoms of CKD can be treated for calcification of soft tissue associated with CKD by administering to the subject a therapeutically effective amount of a lanthanum carbonate powder or capsule formulation of the present invention. Calcification can occur in any soft tissue. Soft tissue can include arterial tissue, cardiac muscle, heart valves, joints, skin and breast tissue.

A subject suffering from or having one or more symptoms of secondary hyperparathyroidism can be treated in part by administering to the subject a therapeutically effective amount of a lanthanum carbonate powder or capsule formulation of the present application. Hyperparathyroidism is defined as a disease in a subject having an intact PTH level of about 150 pg/mL or greater (second generation parathyroid hormone assay). The symptoms of late stage hyperparathyroidism include hypocalcaemia (i.e., a blood calcium level below about 8.5 mg/dL), hyperphosphatemia (i.e., a blood phosphate level of above about 4.5 mg/dL), and bone disorders (e.g., bone fractures or bone pain).

Administration of Pharmaceutical Powder and Capsules

The lanthanum carbonate powder and capsule formulations can be orally administered to subjects in accordance with this invention in dosage forms varying from about 125 to about 2000 mg elemental lanthanum as lanthanum carbonate with or immediately after meals. A typical dosage for an adult can be, e.g., 375 mg-6000 mg elemental lanthanum as lanthanum carbonate daily. More preferably, the dosage is 375-3750 mg/day. The dose can be divided and taken with each meal, for example a 250, 500, 750, or 1000 mg sachet or a 250, 375, or 500 mg capsule, e.g., three times per day. Serum phosphate levels can be monitored weekly and dosages can be modified until an optimal serum phosphate level is reached. Administration may be conducted in an uninterrupted regimen; such a regimen may be a long term regimen, e.g., a permanent regimen, for treating chronic conditions. Capsules can be chewed like a tablet or, for patients who have difficulty chewing, capsules can be opened and the contents can be sprinkled onto the tongue or onto food. Alternatively, capsules can be swallowed whole. Powders can also be sprinkled onto the tongue or onto food or mixed with small amounts of water or soft drinks.

The bioavailability (percentage of the dose absorbed unchanged into the plasma) of lanthanum after administration of a formulation is very low (i.e., approximately 0.001%), corresponding to average maximum plasma concentrations ($C_{max}$) of up to approximately 0.7 ng/mL and average AUC (area under the plasma concentration-time curve) of up to approximately 24 ng·h/mL in healthy volunteers at steady state after typical doses of 1000 mg tid administered by lanthanum carbonate chewable tablets, with corresponding values in dialysis patients being approximately 1.1 ng/mL and approximately 31 ng·h/mL, respectively). Typically, $T_{max}$ (time of first achievement of $C_{max}$) values are essentially unaffected by dose and $C_{max}$ and AUC values vary linearly with dosage for oral dosages up to about 1500 mg/day. Typically, $C_{max}$ and AUC values plateau for dosages above about 1500 mg/day. As plasma concentrations of lanthanum are a surrogate safety marker, an alternate formulation should deliver plasma lanthanum concentrations which are not higher, substantially or to a clinically significant extent, than those achieved with comparable doses of the chewable tablet formulation.

It will be understood that the type of lanthanum carbonate formulation and the duration of the treatment will vary depending on the requirements for treatment of individual subjects. The precise dosage regimen will be determined by the attending physician or veterinarian who will, inter alia, consider factors such as body weight, age and specific symptoms. The physician or veterinarian may titrate the dosage of lanthanum carbonate administered to a subject to determine the correct dosage for treatment. For example, a physician can measure phosphate levels in a patient, prescribe a particular lanthanum carbonate dosage to the patient for a week, and evaluate after the week if the dosage is appropriate by remeasuring phosphate levels in the patient.

EXAMPLES

Examples 1-12

Compatibility Studies of 500 mg Lanthanum Carbonate Hydrate Immediate Release Capsules Lanthanum carbonate hydrate immediate release capsules were studied to determine their dissolution properties and to ensure that dissolution was unaffected after storage.

Examples 1-3 examine the cause of the decreased dissolution observed after storage of lanthanum carbonate capsules. Based on these experiments it was hypothesized that the gelatin of the capsule shell and the encapsulated magnesium stearate caused the decreased dissolution. Alternative lubricants to magnesium stearate were evaluated in place of magnesium stearate. Examples 4-9, 11, and 12 examine the dissolution properties of capsules containing alternative lubricants to replace magnesium stearate. Example 10 discloses the process for making the capsules tested in Examples 11 and 12.

Examples 1-9, 11, and 12 below each used the following dissolution method for determining the dissolution rate for lanthanum carbonate contained in 500 mg lanthanum carbonate hydrate immediate release capsules.

Preparation of Solutions

Preparation of Dissolution Medium (0.25 M HCl)

For the preparation of 10 liters of 0.25 M HCl, 232.5 mL of HCl 37% (available from Merck, Darmstadt, Germany) was transferred into a 10 L volumetric flask and filled to volume using deionized water. The volume was scaled depending on requirements.

Urotropin Solvent (1 mol/L) (hexamine)

35.0 g urotropin (hexamethylenetetramine) (available from VWR, West Chester, Pa.) was dissolved in a 250 mL volumetric flask filled to volume with purified water.

Sodium Acetate Buffer pH 6.2 (0.2 mol/L)

16.4 g sodium acetate (available from Merck, Darmstadt, Germany) was dissolved in a 1000 mL volumetric flask filled to volume with purified water and adjusted to pH 6.2 with acetic acid (available from Merck, Darmstadt, Germany).

Xylenol Orange Indicator Solution 10 mg Xylenol orange tetra sodium salt (available from Merck, Darmstadt, Germany) was dissolved in 5 mL ethanol (available from Merck, Darmstadt, Germany) in a 10 mL volumetric flask and diluted to volume using purified water. The solution expired after 1 week.

Disodium EDTA (0.001 Mol/L) Volumetric Standard Solution

The volumetric standard solution was prepared using a 1/10 volumetric dilution of commercially available standardized 0.01 mol/L EDTA (available from Fluka/Sigma Aldrich, St. Louis, Mo.).

Measuring Capsule Dissolution over Time

A Sotax AT7 Smart (available from Sotax, Hopkinton, Mass.) with 6×900 mL dissolution vessels, 6 corresponding paddles (USP Type II at 50 rpm), and a Whatman GF/D (2.7 μm glass fiber) filter that complied with USP Apparatus 2 and JP Method 2 requirements were used to perform the dissolution. 900 mL of dissolution medium was allowed to equilibrate for at least 30 rain in a dissolution bath at 37° C.±0.5° C. One capsule was then dropped into the dissolution medium. 15 mL of the medium was removed after 5, 10, 15, 30, and 45 minutes using an automatic fraction collector. 15 mL 0.025 M HCL replaced the removed medium at each time point.

To determine the amount of lanthanum ion in the sample, 40 mL of 0.2 mol/L sodium acetate solution pH 6.2 was added to 2.5 mL of removed medium. 0.25 mL of xylenol orange indicator solution was then added and the pH was adjusted to 5.5±0.1 using 1 mol/L hexamine or 0.25 mol/L HCL. The sample was then titrated using 0.001 mol/L disodium EDTA solution from a pink/lilac starting color to a straw color end point. The amount of EDTA solution was correlated to an amount of lanthanum ion in the medium. Lanthanum(III) oxide ($La_2O_3$) (Fluka 04052 available from Sigma Aldrich, St. Louis, Mo.) was used as a reference standard for the amount of lanthanum ion in solution in the titration analysis. Two or three capsules per formulation and condition were generally tested. It was clear from early studies that such small numbers of capsules could reliably show if dissolution rate was affected by the experimental variables under test.

Making the Capsule Formulations Tested in Examples 1-9

Prior to mixing, the ingredients were sieved with a 1.00 mm sieve. The lanthanum carbonate, dextrates (when present), and disintegrant (when present) were mixed for 10 minutes. The colloidal silicon dioxide (when present) was then added and mixed for 2 minutes. Lubricant (when present) was added and mixed for a further 2 minutes. After slugging to obtain a large tablet or roller compacting, the mixture was milled into a coarser powder with better flow properties than the original powders from which the slugs were made. (Unless otherwise stated the mixture was slugged prior to milling.) The mixture was then sieved again with a 1.00 mm sieve.

Hard gelatin capsules were then filled with the lanthanum carbonate powders in an amount equal to 500 mg elemental lanthanum per capsules. Capsugel® (Peapack, N.J.) supplied Coni-Snap® hard gelatin capsules size 00 (0.95 mL volume; 0.917 inches closed length) having the below composition to encapsulate the lanthanum carbonate powders. The body of the capsule shell contained 2 wt % titanium dioxide, 13-16 wt % water, and 82-85 wt % gelatin. The cap of the capsule shell contained 0.1779 wt % indigotine (i.e., FD & C Blue 2), 0.171 wt % erythrosin (i.e., FD & C Red 3), 1.4779 wt % titanium dioxide, 13-16 wt % water, and the remainder being gelatin.

Example 1

Dissolution Profiles for Lanthanum Carbonate Capsules Stored at 60° C. For 2 Weeks Three batches of lanthanum carbonate capsules were manufactured; (1) 900911 made via roller compaction, (2) E341X010, a batch with the same formula as 900911 but made via slugging, and (3) E341X008, a batch made via slugging with crosscarmellose sodium as disintegrant in place of crospovidone.

The dissolution profiles for 3 capsules (E341X008, E341X010, and 910011, number of samples n=2) were determined before and after storage in a drying oven at 60° C. for 2 weeks as shown in FIG. 1. The formulation for each of the 3 capsules is shown in Table 2.

TABLE 2

Formulations tested for their dissolution profiles before and after storage at 60° C. for 2 weeks.

| Formulation E341X008 | | Formulation E341X010 | | Formulation 910011 | |
|---|---|---|---|---|---|
| Name | mg/dosi | Name | mg/dosi | Name | mg/dosi |
| Lanthanum carbonate | 954.0 | Lanthanum carbonate | 954.0 | Lanthanum carbonate | 954.0 |
| Dextrates | 87.7 | Dextrates | 87.7 | Dextrates | 87.7 |
| Colloidal silicon dioxide (Aerosil ® 200) | 11.0 | Colloidal silicon dioxide (Aerosil ® 200) | 11.0 | Colloidal silicon dioxide (Aerosil ® 200) | 11.0 |
| Croscarmellose Sodium | 44.0 | Crospovidone | 44.0 | Crospovidone | 44.0 |
| Magnesium stearate | 3.3 | Magnesium stearate | 3.3 | Magnesium stearate | 3.3 |

As shown in FIG. 1, the dissolution profiles for all capsules after storage at 60° C. for 2 weeks showed a delayed release with a 10 minutes lag time and a lanthanum carbonate dissolution of 35-55% after 45 minutes. Unstressed samples demonstrated a greater than 90% lanthanum carbonate dissolution after 30 minutes.

Capsules from batch number 900911 were also stored for one month at 25° C./60% RH, 30° C./60% RH and 45° C./75% RH. The dissolution rates of the stored capsules at all storage conditions decreased compared to prior to storage. The capsules after storage were less than 80% dissolved after 30 minutes.

Example 2

Dissolution Profiles for Compacted (i.e., Slugged) and Encapsulated Lanthanum Carbonate

TABLE 3

Formulation for testing preparation methods
Formulation E341X018

| Name | mg/dosi |
|---|---|
| Lanthanum carbonate | 954.0 |
| Dextrates | 87.7 |
| Colloidal silicon dioxide (Aerosil ® 200) | 11.0 |
| Crospovidone | 44.0 |
| Magnesium stearate | 3.3 |

Figure 2:
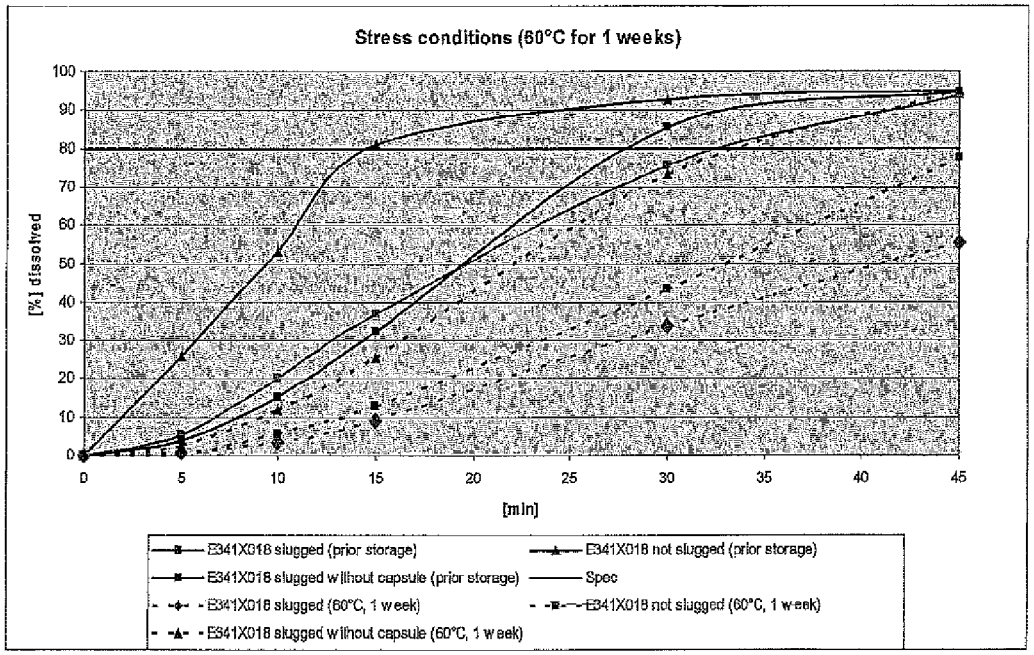
FIG. 2 is a graph comparing the dissolution rates before and after storage at 60° C. for 1 week of (1) a formulation that was slugged and encapsulated before storage, (2) a formulation that was not slugged, but encapsulated before storage, and (3) a formulation that was slugged before storage and encapsulated after storage.

To determine whether slugging or encapsulation affected dissolution rates, three different preparations based on formulation batch E341X018 (Table 3) were produced: (1) a formulation that was slugged and encapsulated prior to storage, (2) a formulation that was not slugged, but encapsulated prior to storage, and (3) a formulation that was slugged prior to storage and encapsulated after storage. The three preparations before and after storage in a drying oven at 60° C. for 1 week were tested for their dissolution properties (number of samples n=3). The dissolution profiles for the preparations before and after storage are displayed in FIG. 2.

Although storage delayed dissolution of each of the preparations compared to before storage, the slugged, unencapsulated prior to storage preparation was less affected by storage than the slugged, encapsulated preparation and the unslugged, encapsulated preparation. These results suggest that the gelatin capsule shell may contribute to the decreased dissolution rate.

Example 3

Impact of a Single Ingredient on the Dissolution Profile of Lanthanum Carbonate Capsules To determine whether a single ingredient in the capsule formulation affected dissolution rates, the dissolution profiles of formulations missing a single ingredient before and after storage in a drying oven at 60° C. for 1 week were determined. The base formulation, prior to removal of ingredients, is shown in Table 4.

TABLE 4

Base formulation prior to removal of ingredients
Basis Formulation

| Name | mg/dosi |
|---|---|
| Lanthanum carbonate | 954.0 |
| Dextrates | 87.7 |
| Colloidal silicon dioxide (Aerosil ® 200) | 11.0 |
| Crospovidone | 44.0 |
| Magnesium stearate | 3.3 |

Figure 3:
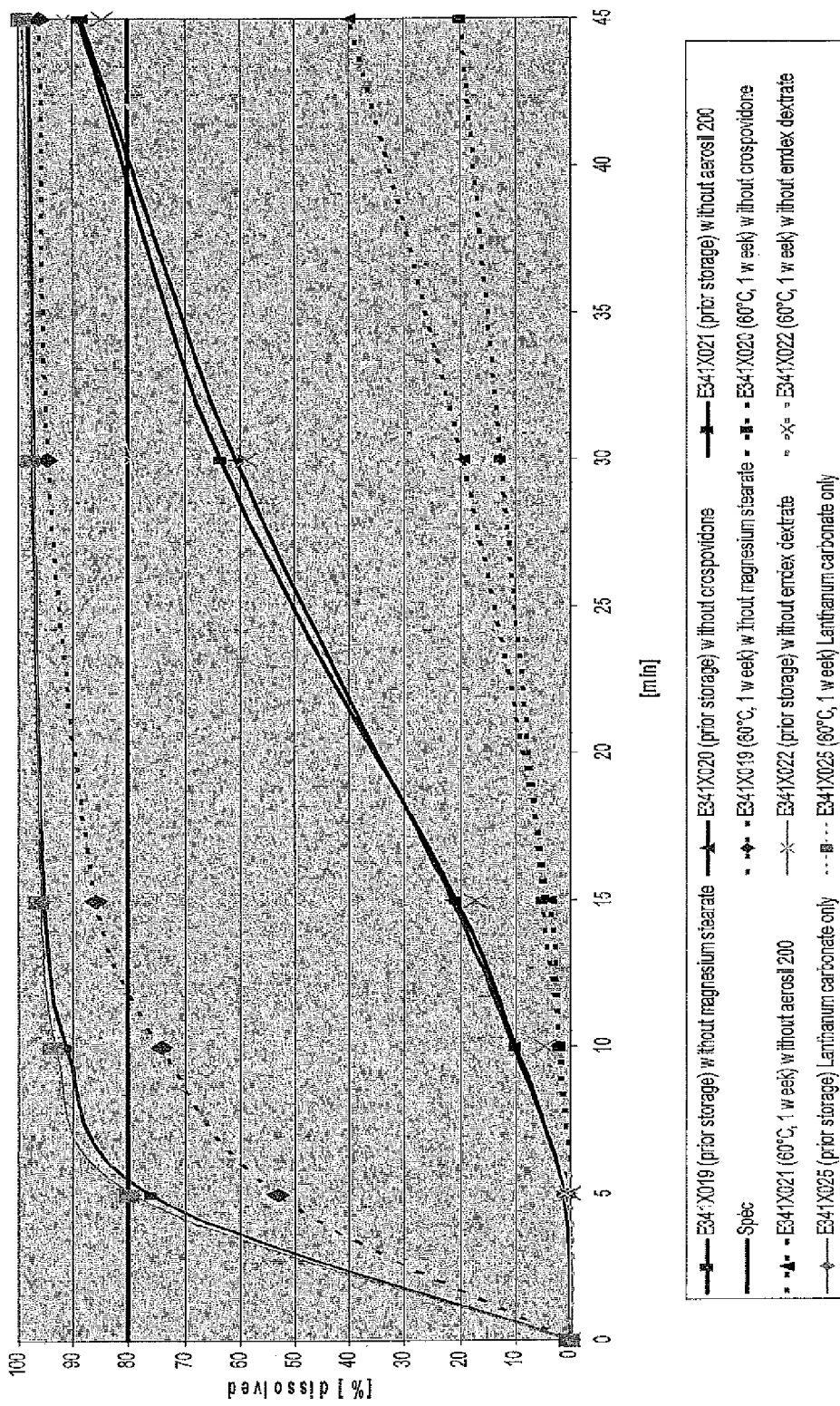
FIG. 3 is a graph comparing the dissolution profiles before and after storage at 60° C. for 1 week for the following formulations: (1) a formulation without magnesium stearate, (2) a formulation without colloidal silicon dioxide, (3) a formulation containing only lanthanum carbonate, (4) a formulation without crospovidone, and (5) a formulation without dextrates.

FIG. 3 provides the dissolution profiles before and after storage for the following formulations: (1) a formulation without magnesium stearate, (2) a formulation without colloidal silicon dioxide, (3) a formulation containing only lanthanum carbonate, (4) a formulation without crospovidone, and (5) a formulation without dextrates.

Formulations without magnesium stearate both prior to and after storage showed relatively fast dissolutions. The dissolution curves for formulations containing only lanthanum carbonate before and after storage were overlapping. Formulations without dextrates showed a delayed release profile with a lag of 5 minutes both before and after storage. Formulations without colloidal silicon dioxide and formulations without crospovidone both demonstrated a delayed release dissolution profile with a lag of 5 minutes prior to storage and a delayed release dissolution profile with a lag of 10 minutes after storage. All the formulations containing magnesium stearate had reduced dissolution rates after storage and it was deduced that the presence of magnesium stearate and the gelatin capsule shell were together responsible for the reduction in dissolution rate during storage.

Example 4

Dissolution Profiles for Lanthanum Carbonate Capsules Containing Magnesium Stearate, Glycerol Behenate, or Sodium Stearyl Fumarate Alternative lubricants were tested to determine their effect on the dissolution of lanthanum carbonate capsules before and after storage. As shown in Table 5, 4 formulations were tested: (1) a formulation containing magnesium stearate, (2) a formulation without a lubricant, (3) a formulation containing glycerol behenate instead of magnesium stearate, and (4) a formulation containing sodium stearyl fumarate instead of magnesium stearate.

TABLE 5

Formulations tested for their dissolution profiles before and after storage in a drying oven at 60° C. for 1 week.

| Name | mg/dosi | Name | mg/dosi |
|---|---|---|---|
| Formulation E341X018 | | Formulation E341X019 | |
| Lanthanum carbonate | 954.0 | Lanthanum carbonate | 1908.0 |
| Dextrates | 87.7 | Dextrates | 87.7 |
| Colloidal silicon dioxide (Aerosil ® 200) | 11.0 | Colloidal silicon dioxide (Aerosil ® 200) | 11.0 |
| Crospovidone | 44.0 | Crospovidone | 44.0 |
| Magnesium stearate | 3.3 | Magnesium stearate | 0.0 |
| Formulation E341X023 | | Formulation E341X024 | |
| Lanthanum carbonate | 954.0 | Lanthanum carbonate | 954.0 |
| Dextrates | 76.7 | Dextrates | 76.7 |
| Colloidal silicon dioxide (Aerosil ® 200) | 11.0 | Colloidal silicon dioxide (Aerosil ® 200) | 11.0 |
| Crospovidone | 44.0 | Crospovidone | 44.0 |
| Glycerol behenate | 11.0 | Sodium stearyl fumarate | 11.0 |

Figure 4:
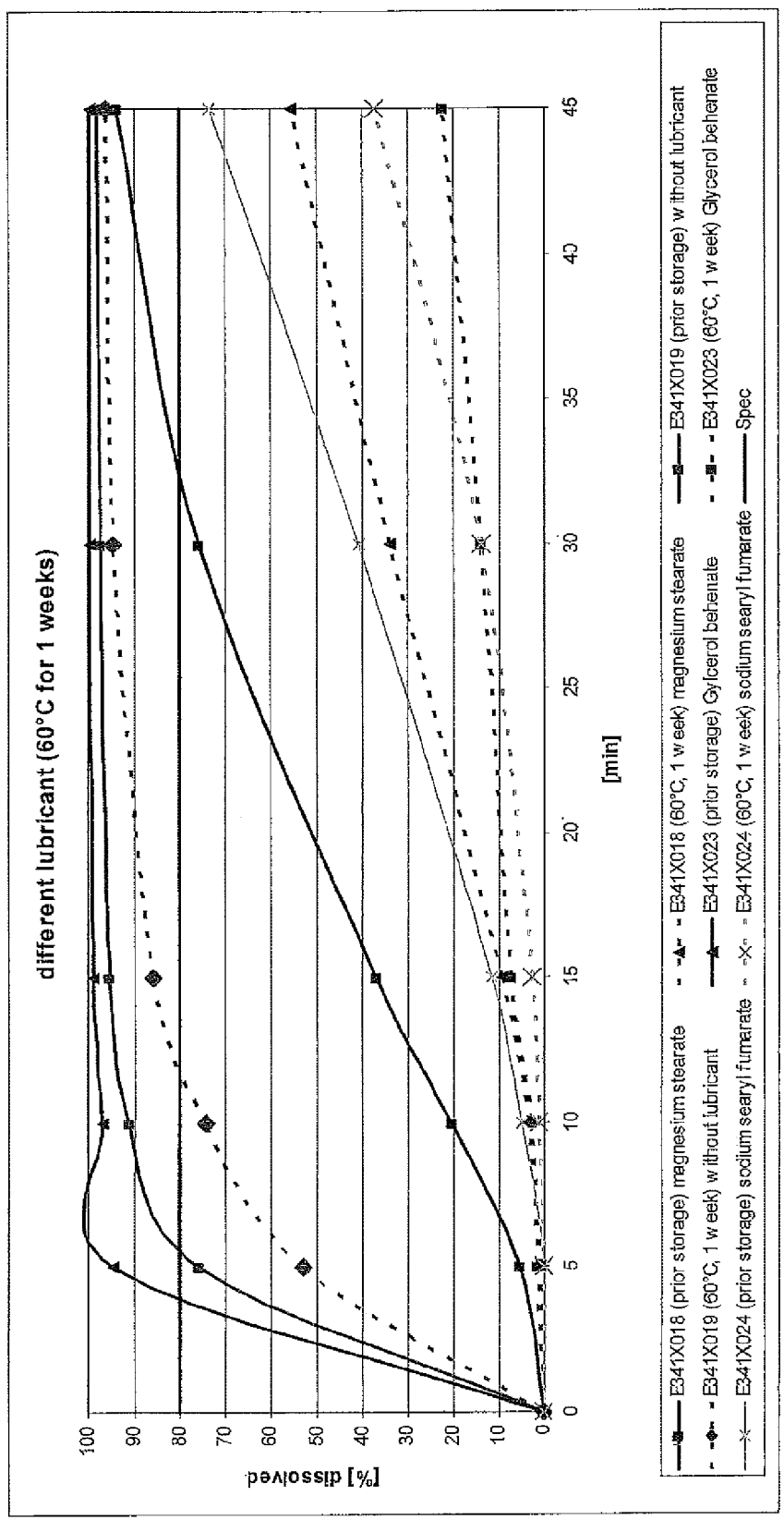
FIG. 4 is a graph comparing the dissolution profiles before and after storage at 60° C. for 1 week for the following formulations: (1) a formulation containing magnesium stearate, (2) a formulation without a lubricant, (3) a formulation containing glycerol behenate instead of magnesium stearate, and (4) a formulation containing sodium stearyl fumarate instead of magnesium stearate.

FIG. 4 discloses the dissolution curves for formulations containing different lubricants before and after storage in a drying oven at 60° C. for 1 week. Formulations containing magnesium stearate and formulations containing glycerol behenate had relatively fast dissolution profiles prior to storage and delayed release dissolution profiles with a lag of 5 minutes after storage. Formulations without a lubricant dissolved relatively fast both before and after storage. Formulations containing sodium stearyl fumarate had a delayed release dissolution profile with a lag of 5 minutes before storage and a delayed release dissolution profile with a lag of 10 minutes after storage.

Example 5

Dissolution Profiles for Lanthanum Carbonate Capsules Containing PEG 6000, L-Leucine, L-Leucine/PEG 6000, or Talc Alternative lubricants were tested to determine their effect on the dissolution of lanthanum carbonate capsules before and after storage in a drying oven at 60° C. for 1 week. As shown in Table 6, 4 formulations were tested each with a different lubricant: polyethyleneglycol, L-leucine, L-leucine/PEG 6000, or talc. The L-leucine/PEG 6000 lubricant is a mixture of 60 wt % L-leucine (available from Sigma-Aldrich, St. Louis, Mo.) and 40 wt % PEG 6000 (available from Croda, East Yorkshire, UK).

TABLE 6

Formulations tested for their dissolution profiles before and after storage at 60° C. for 1 week.

| Formulations | |
|---|---|
| Name | mg/dosi |
| Lanthanum carbonate | 954.0 |
| Dextrates | 0.0 |
| Colloidal silicon dioxide (Aerosil ® 200) | 0.0 |
| Crospovidone | 0.0 |
| PEO 6000, L-leucine, L-leucine/PEG 6000, or talc | 55.0 |

FIG. 5 discloses the dissolution curves for formulations containing different lubricants before and after storage in a drying oven at 60° C. for 1 week. Formulations containing PEG 6000 had a relatively fast dissolution profile prior to storage and showed no significant release after storage. Formulations containing L-leucine and formulations containing a mixture of L-leucine and PEG 6000 had a relatively fast dissolution profile prior to storage and showed a delayed release with a lag of 5 minutes after storage. Formulations containing talc had relatively fast dissolution profiles both before and after storage.

Example 6

Dissolution Profiles for Lanthanum Carbonate Capsules Containing LUBRITAB® or CUTINA® HR Alternative lubricants were tested to determine their affect on the dissolution of lanthanum carbonate capsules before and after storage in a drying oven at 60° C. for 1 week. As shown in Table 7, 2 formulations were tested each with a different lubricant: LUBRITAB® (hydrogenated vegetable oil and hydrogenated oil; available from J. Rettenmaier & Söhne GMBH+CO.KG, Rosenberg, Germany) or CUTINA® HR (hydrogenated castor oil; available from Cognis, Cincinnati, Ohio).

TABLE 7

Formulations tested for their dissolution profiles before and after storage at 60° C. for 1 week.

| Formulations | |
|---|---|
| Name | mg/dosi |
| Lanthanum carbonate | 954.0 |
| Dextrates | 0.0 |
| Colloidal silicon dioxide (Aerosil ® 200) | 0.0 |
| Crospovidone | 0.0 |
| LUBRITAB ® or CUTINA ® HR | 55.0 |

Figure 6:
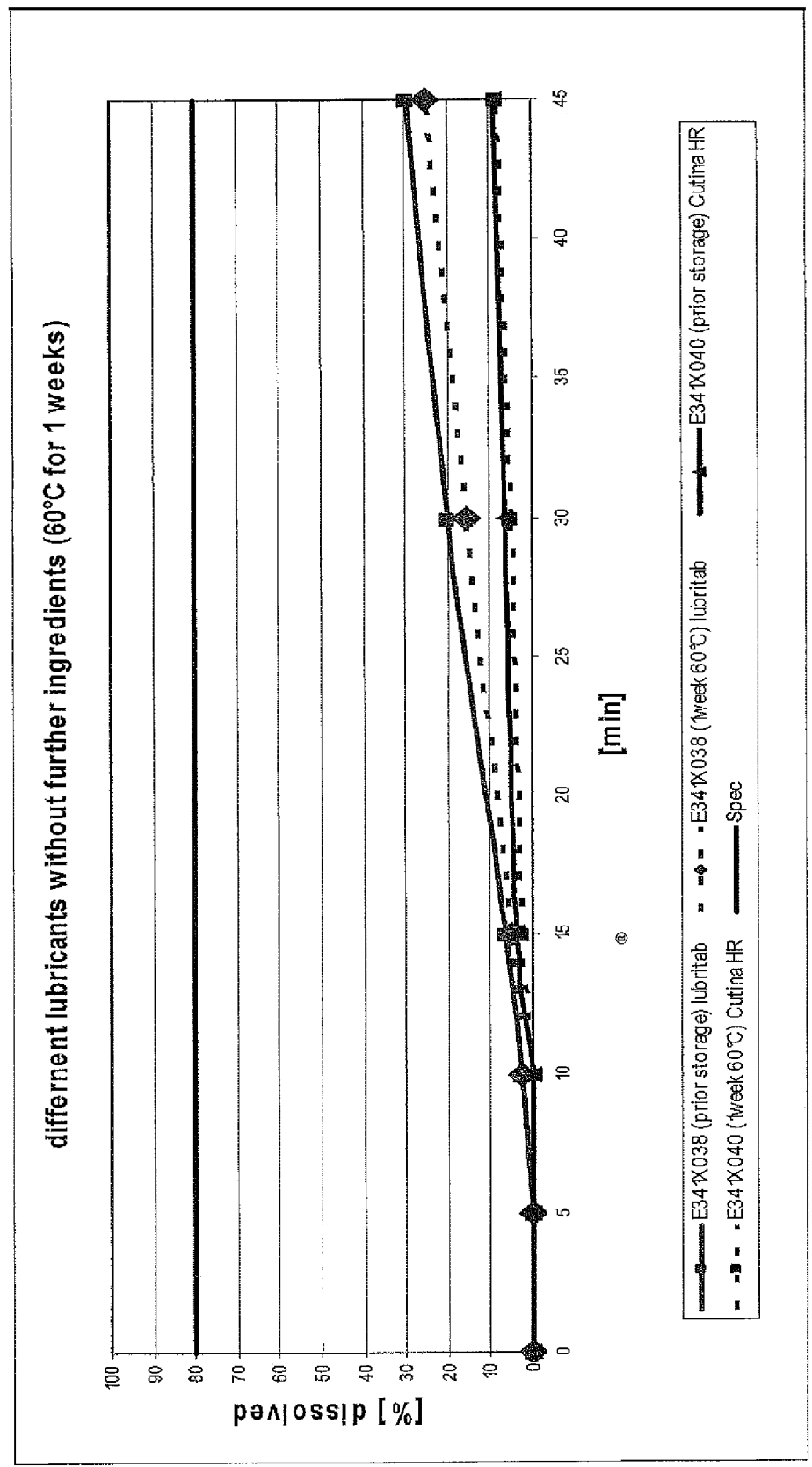
FIG. 6 is a graph comparing the dissolution profiles before and after storage at 60° C. for 1 week for the following formulations: (1) a formulation containing LUBRITAB® and (2) a formulation containing CUTINA® HR.

FIG. 6 discloses the dissolution curves for formulations containing different lubricants before and after storage at 60° C. for 1 week. Formulations containing LUBRITAB® had a delayed release profile with a lag of 5 minutes before and after storage although storage caused a more delayed release over time. Formulations containing CUTINA® HR tested before and after storage had similar delayed release profiles with a lag of 10 minutes.

Example 7

Dissolution Profiles for Lanthanum Carbonate Capsules Containing Either Dextrates, Colloidal Silicon Dioxide, Crospovidone, and L-Leucine or Only L-Leucine Lanthanum carbonate capsules containing either dextrates, colloidal silicon dioxide, crospovidone, and L-leucine or only L-leucine were tested to determine their affect on the dissolution of lanthanum carbonate capsules before and after storage in a drying oven at 60° C. for 1 week. As shown in Table 8, 2 formulations were tested.

TABLE 8

Formulations tested for their dissolution profiles before and after storage at 60° C. for 1 week.

| Formulation E341X030 | | Formulation E341X031 | |
|---|---|---|---|
| Name | mg/dosi | Name | mg/dosi |
| Lanthanum carbonate | 954.0 | Lanthanum carbonate | 954.0 |
| Dextrates | 0.0 | Dextrates | 36.0 |
| Colloidal silicon dioxide (Aerosil ® 200) | 0.0 | Colloidal silicon dioxide (Aerosil ® 200) | 11.0 |
| Crospovidone | 0.0 | Crospovidone | 44.0 |
| L-Leucine | 55.0 | L-Leucine | 55.0 |

Figure 7:
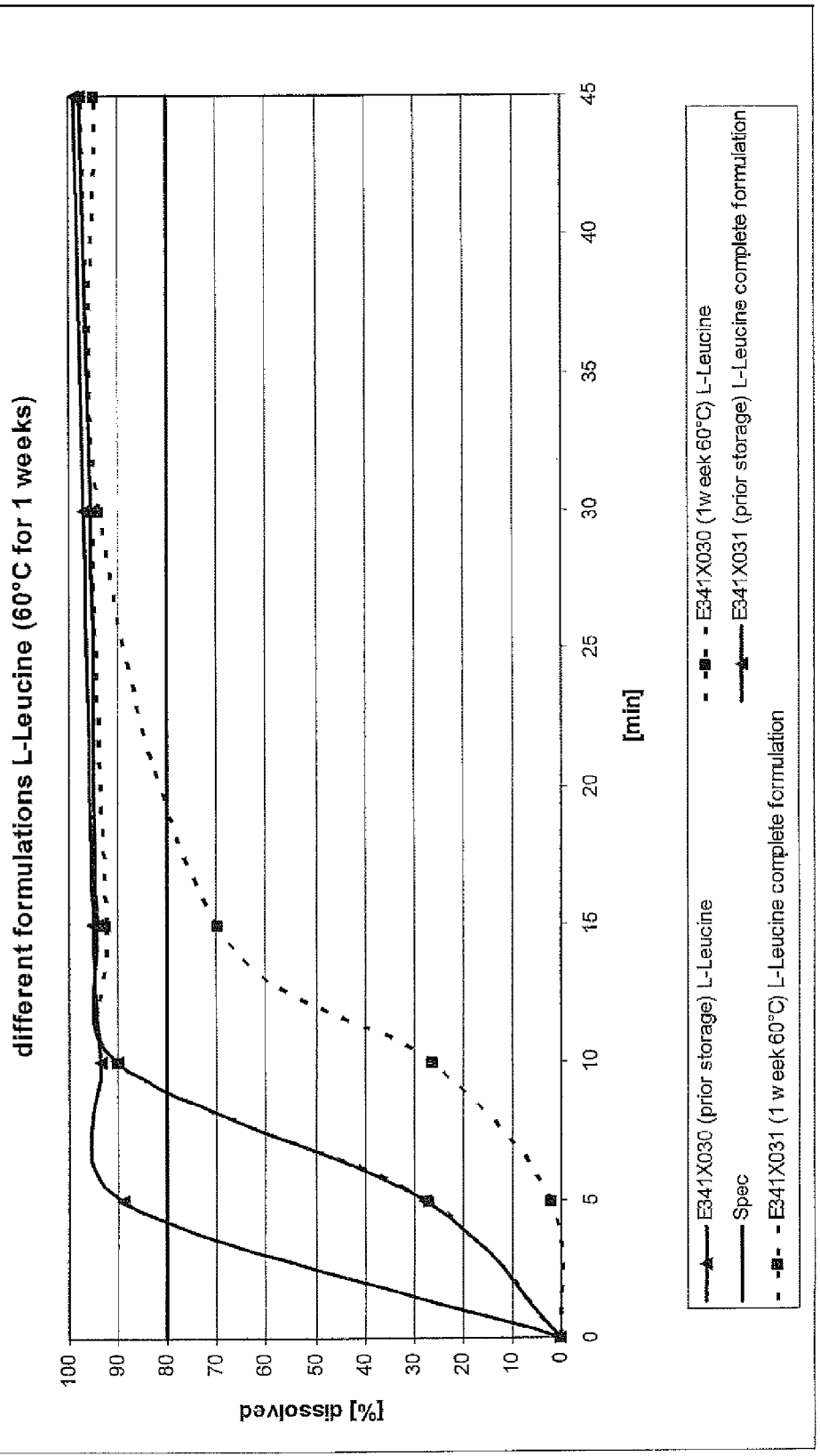
FIG. 7 is a graph comparing the dissolution profiles before and after storage at 60° C. for 1 week for the following formulations: (1) a lanthanum carbonate formulation containing only L-leucine and (2) a lanthanum carbonate formulation containing dextrates, colloidal silicon dioxide, crospovidone, and L-leucine.

FIG. 7 discloses the dissolution curves for the 2 formulations before and after storage at 60° C. for 1 week. Lanthanum carbonate formulations containing only L-leucine had a relatively fast release profile before storage and had a delayed release profile with a lag of 5 minutes after storage. Lanthanum carbonate formulations containing dextrates, colloidal silicon dioxide, crospovidone, and L-leucine after storage released at a slower rate compared to before storage.

Example 8

Dissolution Profiles for Lanthanum Carbonate Capsules Containing PEG 6000 Before and after Storage at 60° C. for 1 Week or 50° C. for 1 Week Lanthanum carbonate capsules containing PEG 6000 were tested to determine their dissolution before and after storage at 60° C. for 1 week or 50° C. for 1 week. As shown in Table 9, the following formulation was tested.

TABLE 9

Formulation tested for its dissolution profiles before and after storage at 60° C. for 1 week or 50° C. for 1 week.

Formulations

| Name | mg/dosi |
|---|---|
| Lanthanum carbonate | 954.0 |
| Dextrates | 0.0 |
| Colloidal silicon dioxide (Aerosil ® 200) | 0.0 |
| Crospovidone | 0.0 |
| PEG 6000 | 55.0 |

Figure 8:
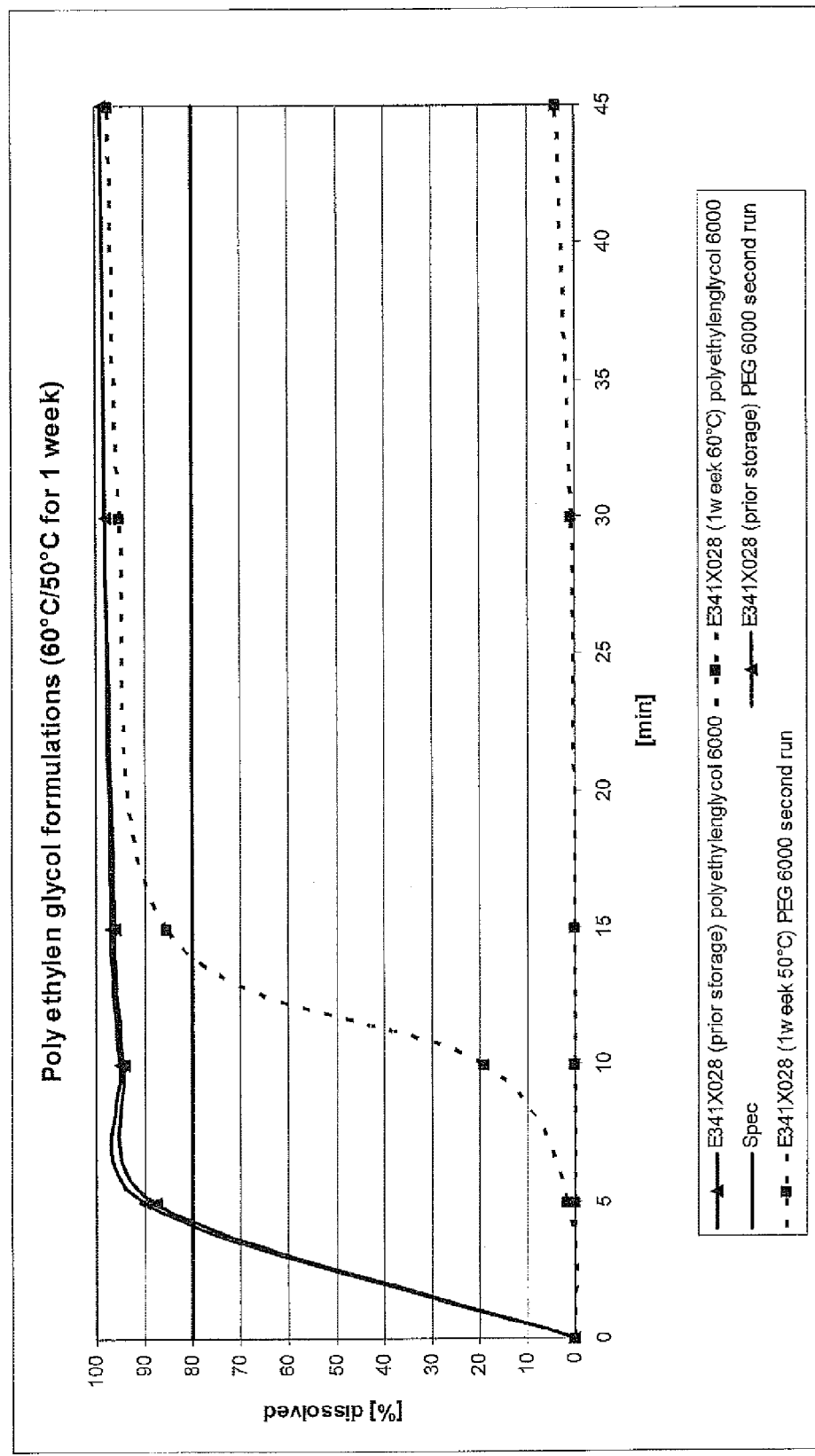
FIG. 8 is a graph comparing the dissolution profiles for lanthanum carbonate capsules containing PEG 6000 before and after storage at 60° C. for 1 week or 50° C. for 1 week.

FIG. 8 discloses the dissolution curves for the formulation before and after storage at 60° C. for 1 week or 50° C. for 1 week. Testing at 50° C. was performed since the melting point of PEG 6000 is 55° C. Formulations prior to storage showed a relatively fast dissolution profile. Formulations after storage at 50° C. for 1 week showed a delayed release with a lag of 5 minutes while formulations after storage at 60° C. for 1 week showed no significant release.

Example 9

Dissolution Profiles for Lanthanum Carbonate Capsules Containing Either Dextrates, Colloidal Silicon Dioxide, Crospovidone, and Talc or Only Talc Lanthanum carbonate capsules containing dextrates, colloidal silicon dioxide, crospovidone, and talc were tested to determine their dissolution before and after storage in a drying oven at 60° C. for 1 or 2 weeks. Lanthanum carbonate capsules containing only talc were tested to determine their dissolution before and after storage at 60° C. for 1 week. As shown in Table 10, the following formulations were tested.

TABLE 10

Formulations tested for their dissolution profiles before and after storage at 60° C. for 1 or 2 weeks.

| Formulation E341X034 | | Formulation E341X035 | |
|---|---|---|---|
| Name | mg/dosi | Name | mg/dosi |
| Lanthanum carbonate | 954.0 | Lanthanum carbonate | 954.0 |
| Dextrates | 0.0 | Dextrates | 36.0 |
| Colloidal silicon dioxide (Aerosil ® 200) | 0.0 | Colloidal silicon dioxide (Aerosil ® 200) | 11.0 |
| Crospovidone | 0.0 | Crospovidone | 44.0 |
| Talc | 55.0 | Talc | 55.0 |

Figure 9:
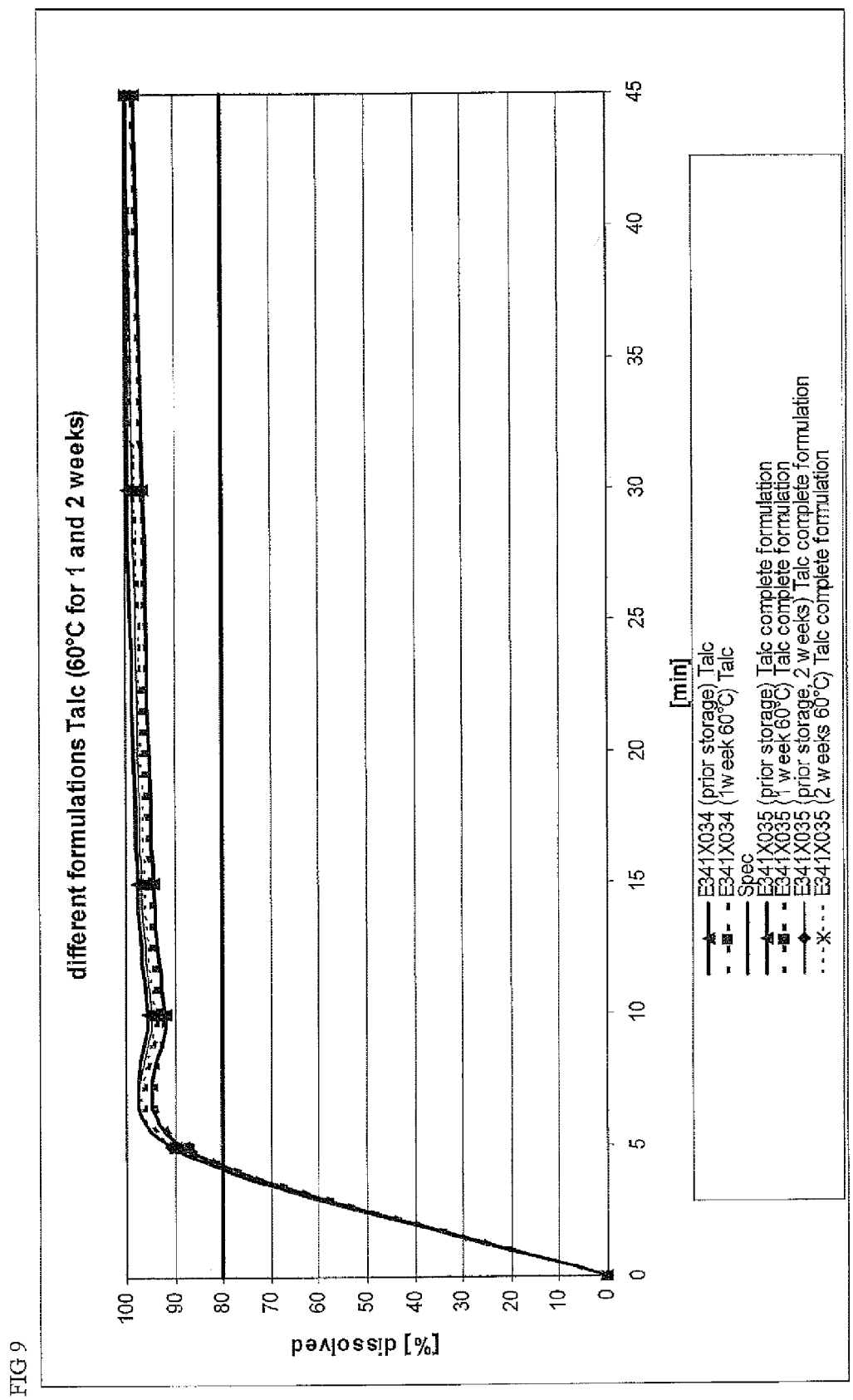
FIG. 9 is a graph comparing the dissolution profiles for lanthanum carbonate capsules containing dextrates, colloidal silicon dioxide, crospovidone, and talc before and after storage at 60° C. for 1 or 2 weeks and for lanthanum carbonate capsules containing only talc before and after storage at 60° C. for 1 week.

FIG. 9 discloses the dissolution curves for the formulations before and after storage at 60° C. for 1 or 2 weeks. All formulations prior to and after storage provided relatively fast dissolution profiles. Talc is a temperature stable lubricant for lanthanum carbonate capsules.

Example 10

Manufacturing of Lanthanum Carbonate Capsules Containing Talc

TABLE 11

Ingredients for the Lanthanum Carbonate Capsule

| Ingredient | batch | amount | % (wt/wt) |
|---|---|---|---|
| Lanthanum carbonate | 1845634 | 954.0 mg | 86.7 |
| Dextrates (Emdex ®) | 474620 | 90.7 mg | 8.2 |
| Colloidal silicon dioxide (Aerosil ® 200) | 1926183 | 11.0 mg | 1.0 |
| Crospovidone | 2200764 | 44.0 mg | 4.0 |
| Talc | 1910860 | 0.275 mg | 0.025 |

The ingredients in Table 11 were weighed to a batch size of 104.5 kg and sieved with a 1 mm hand sieve. Lanthanum carbonate, dextrates and crospovidone were then blended for 10 min on a tumble blender. The colloidal silicon dioxide was then added and blended for a further 2 minutes at 6 rpm and finally the talc was added and blended for a further 2 minutes at 6 rpm.

The blend was then compacted on a compactor (Bepex Pharmapaktor L 200/50 P, Hosokawa Micron Ltd., UK). The compaction was performed in 2 sub-batches of about 41 Kg for sub-batch 1 (batch no.: E341X043) and about 56 kg for sub-batch 2 (batch no.: E341X044) using two different settings for the roller compression force to optimize the process parameter. Both compaction settings produced properly compacted material. Table 12 lists the different settings.

TABLE 12

Compactor Settings

| | Setting 1 | Setting 2 |
|---|---|---|
| Screw size | 3 | 3 |
| Screw rotation (rpm) | 48 | 77 |
| Roller compression force (k/N) | 29 | 35 |
| Roller type (corrugated) | 4.1 | 4.1 |
| Roller rotation (rpm) | 7.7 | 12.2 |
| Sieve size (mm) | 1.25 | 1.25 |
| Sieve rotation (rpm) | 56 | 77 |

Physical characteristics of the blend as shown in Table 13 were determined.

TABLE 13

Physical Characteristics of Final Blend

| | Method | Results Setting 1 (E341X043) | | Results Setting 2 (E341X044) | |
|---|---|---|---|---|---|
| Bulk density | Ph.Eur. 2.9.15 | 1.000 | | 0.980 | |
| Tapped density | Ph.Eur. 2.9.15 | 1.282 | | 1.250 | |
| Hausner-ratio | — | 1.282 | | 1.275 | |
| Particle Size distribution | Ph.Eur. 2.9.16 | <63 µm | 23.3% | <63 µm | 15.4% |
| | | 63-90 µm | 11.9% | 63-90 µm | 10.6% |
| | | 90-125 µm | 9.8% | 90-125 µm | 13.8% |
| | | 125-250 µm | 18.0% | 125-250 µm | 18.9% |
| | | 250-500 µm | 21.6% | 250-500 µm | 23.0% |
| | | 500-710 µm | 11.7% | 500-710 µm | 12.3% |
| | | 710-1000 µm | 3.7% | 710-1000 µm | 5.9% |
| | | 1000-1250 µm | 0.2% | 1000-1250 µm | 0.1% |
| | | >1250 µm | 0.0% | >1250 µm | 0.0% |

The material processed on setting 2 showed a lower amount of fine particles which could be an advantage for the filing of capsules. There are no significant differences between Bulk and tapped density.

Both final blends in an amount equal to 500 mg elemental lanthanum were filled into Coni-Snap® hard gelatine capsules size 00 (available from Capsugel®, Peapack, N.J.) using a capsule filler (GKF 1500 or KKE 1500 available from Bosch, Brooklyn Park, Minn.). For the purpose of evaluation of process robustness, two different speeds for the filler were used (90 cycles/min and 100 cycles/min) The machine runs steadily with both speeds but capsule filling runs more smoothly with compaction setting 2 in comparison with compaction setting 1.

Example 11

Dissolution Testing of Lanthanum Carbonate Capsules Containing Talc

Figure 10:
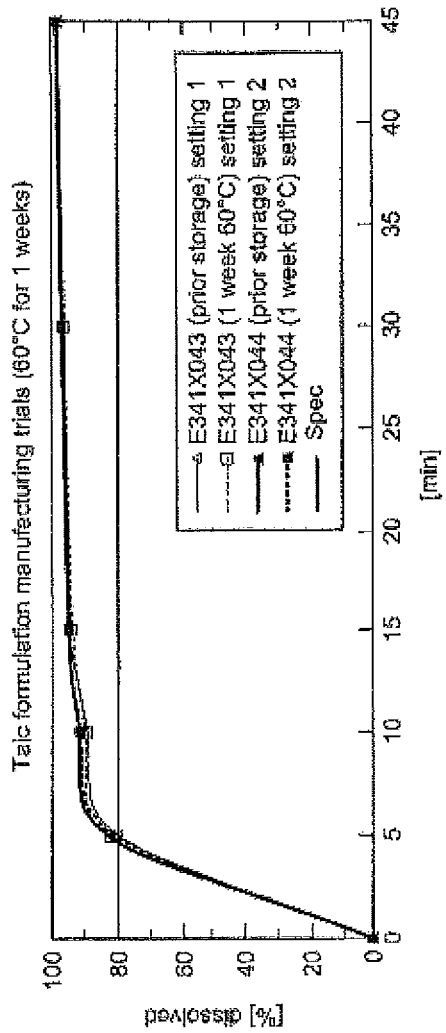
FIG. 10 is a graph comparing the dissolution profiles for lanthanum carbonate capsules containing dextrates, colloidal silicon dioxide, crospovidone, and talc before and after storage at 60° C. for 1 week.

The capsules (E341X043 and E341X044) were stored at room temperature and in stressed conditions in a drying oven at 60° C. for one week and were tested for their dissolution properties. The results are presented in Table 14 and FIG. 10.

TABLE 14

Tablet dissolution results for tablets stored at room temperature and at 60° C. for 1 week

| Dissolution time point | Batch E341X043 | | Batch E341X044 | |
|---|---|---|---|---|
| [min] | Room temperature | One week at 60° C. | Room temperature | One week at 60° C. |
| 5 | 79.8 | 82.2 | 83.3 | 80.7 |
| 10 | 89.2 | 89.6 | 91.6 | 91.4 |
| 15 | 94.6 | 93.7 | 95.3 | 95.2 |
| 30 | 96.8 | 96.0 | 97.6 | 97.4 |
| 45 | 98.6 | 98.4 | 99.2 | 98.8 |

All dissolution profiles fulfilled the specification of greater than 80% lanthanum carbonate dissolution after 30 minutes. A decreasing of the dissolution rate after storage for one week at 60° C. in comparison with room temperature was not evident. The results showed no significant difference between the two batches. The results showed that the talc can be used as lubricant for manufacturing of lanthanum carbonate capsules with no significant effect on the dissolution rate compared to the storage condition.

Example 12

Long Term Stability Testing of Lanthanum Carbonate 500 mg Capsules

Capsules were manufactured according to Example 10 and placed on a long term stability test. Table 15 provides stability data after 4 weeks.

TABLE 15

Stability Data for Lanthanum Carbonate 500 mg Capsules; Lot 1005001; 200 mL HDPE Bottle with Polypropylene Closure, 90 Count

| Storage Time | Appearance | Lanthanum Assay (%) | Moisture (% w/w) | Lanthanum Hydroxycarbonate Polymorph I | Polymorph II | Dissolution (%) |
|---|---|---|---|---|---|---|
| Specification | Hard gelatin capsule with opaque purple cap printed S405, opaque white body printed 500 mg and containing a white to off-white granulate. | 90-110% | Record | Not more than 1.8% | Not more than 2.0% | Q = 80% after 30 minutes |
| Initial 25° C./60% RH | Complies | 98.2 | 1.6 | Complies | Complies | 97 |
| 4 weeks 30° C./75% RH | Complies | 99.5 | 1.7 | Complies | Complies | 97 |
| 4 weeks 40° C./75% RH | Complies | 99.4 | 1.6 | Complies | Complies | 97 |
| 4 weeks | Complies | 98.6 | 1.2 | Complies | Complies | 95 |

Data showed no change or essentially no change in the percent dissolution after 30 minutes in 0.25 M HCl after storage at 25° C./60% RH 30° C./75% RH, or 40° C./75% RH for 4 weeks. Capsules from this batch are used in a clinical study to evaluate the bioavailability of lanthanum carbonate from capsules relative to that from tablets.

Examples 13 and 14

Pharmacodynamic Equivalence Studies for Lanthanum Carbonate for Formulations

These examples describe results from pharmacodynamic equivalence studies to compare the delivery of lanthanum to and availability of lanthanum in the gastrointestinal tract and its absorption into the systemic circulation (blood plasma) from capsule or oral powder formulations with those from the chewable tablet. These studies are conducted in healthy volunteers who do not have elevated serum phosphate concentrations. Hence, the efficacy of lanthanum carbonate in reducing serum phosphate concentrations, which would be the usual primary endpoint in a clinical study in ESRD patients on dialysis, cannot be used in healthy volunteer studies. Urinary phosphate excretion is an alternative measure which can be used in healthy volunteers to assess the impact of a phosphate binder on phosphate absorption from a standard meal and this is the primary endpoint in pharmacodynamic equivalence studies: the higher the urinary phosphate excretion, the higher the extent of phosphate absorption. Hence the formulations are compared with respect to the extents of their effects on urinary phosphate excretion, which are assessed against equivalence acceptance criteria. In addition, plasma lanthanum concentrations are compared as a secondary objective, since lanthanum systemic exposure is a surrogate safety marker.

Example 13

A Phase 1 Pharmacodynamic Equivalence Study Comparing Urinary Phosphate Excretion and Plasma Lanthanum Pharmacokinetics for a Lanthanum Carbonate Capsule Formulation, a Lanthanum Carbonate Opened Capsule Formulation, and Chewable Lanthanum Carbonate Tablets Administered to Healthy Adult Subjects Objectives: Primary
To compare the average daily urinary phosphate excretion over 3 days following dosing between a lanthanum carbonate capsule formulation (Formulation A) and a lanthanum carbonate chewable tablet formulation (Formulation C), administered as 1000 mg 3 times per day with apple-sauce, immediately following meals.
Objectives: Secondary
(1) To compare the average daily urinary phosphate excretion over 3 days following dosing between lanthanum carbonate opened capsules (Formulation B) and lanthanum carbonate chewable tablet formulations (Formulation C). Each dose was administered as 1000 mg 3 times per day given with apple sauce immediately following meals
(2) To compare the urinary phosphate excretion on Day 4 following 3 days of dosing of the lanthanum carbonate capsule formulation (Formulation A), the opened capsule formulation (Formulation B), and the chewable tablet formulation (Formulation C).

(3) To assess the safety and tolerability of the lanthanum carbonate capsule formulation (Formulation A), the opened capsule formulation (Formulation B), and chewable tablet formulation (Formulation C).
(4) To compare the lanthanum pharmacokinetic (PK) profiles of the lanthanum carbonate capsule formulation (Formulation A) and the opened capsule formulation (Formulation B) with the lanthanum carbonate chewable tablet formulation (Formulation C).
Study Design
A randomized, open-label, 3-period crossover study was performed in healthy male and female volunteers (aged 18-55 years at the time of consent) conducted at a single study center. There was a screening period followed by 3 dosing periods for each subject. There was a washout period of at least 14 days between dosing periods. Subject were randomised to a dosing sequence where they received 1 of 3 formulations in a random order:
(1) Formulation A, a capsule formulation (2×500 mg/capsules; Coni-Snap® hard gelatine capsules size 00 filled with the formulation of Table 11 manufactured according to Example 10 using a compaction setting similar to Setting 2) in which subjects ingested 1 tablespoon of applesauce immediately after taking each capsule (2 tablespoons of applesauce per dose).
(2) Formulation B, an open capsule formulation (2×500 mg/capsule; the formulation of Table 11 manufactured according to Example 10 using a compaction setting similar to Setting 2 without the capsule) administered by means of the capsule formulation being opened, the contents of each capsule placed on 1 tablespoon of applesauce, the applesauce and contents administered to the subject, and the empty gelatinous capsule discarded, and
(3) Formulation C, chewable tablet formulation (2×500 mg/tablet available as 500 mg Fosrenol® from Shire, Wayne, Pa. containing (1) 954 mg lanthanum carbonate (45.78% wt/wt), (2) 1066.4 mg dextrates (51.17% wt/wt), (3) 42.4 mg colloidal silicon dioxide (2.03% wt/wt), and (4) 21.2 mg magnesium stearate (1.02% wt/wt)) in which subjects also ingested 1 tablespoon of applesauce immediately after taking each tablet (2 tablespoons of applesauce per dose).

Within each period, each formulation was administered 3 times per day following meals for 3 days and following the morning meal of day 4. There were three treatment periods, subjects were randomised to 1 of 6 treatment sequences according to the randomization code, with a wash-out period of at least 14 days between periods.

Sufficient subjects were randomized to ensure a minimum of 72 subjects completed the study.
Criteria for Evaluation
Urine was collected over 24 hour periods as: Day −2 to Day −1; Day −1 to Day 1; Day 1 to Day 2; Day 2 to Day 3 and Day 3 to Day 4. Each collection started within 30 minutes before the morning meal and ended 24 hours later. Urinary phosphate excretion analysis was the primary evaluation for the determination of pharmacodynamic equivalence for this study.

As a secondary evaluation, pharmacokinetic assessments were performed following determination by inductively coupled plasma mass spectrometry of plasma concentrations of lanthanum at the following times: pre-dose (within 30 minutes prior to the start of the morning meal) on Days 1, 2, 3 and 4 and at 3, 4, 5, 6, 8, 12, 18, 24, 36 and 48 hours after the final morning dose on Day 4.
Statistical Methods: Pharmacodynamics
Subjects included in the safety population took at least one dose of lanthanum carbonate and had at least one post-dose safety assessment. The pharmacodynamic population included all evaluable subjects from the safety population with no major protocol deviations, including all subjects in the safety population who completed all urine collections and consumed at least 95% of food in all treatment periods. Subjects who vomited between days −2 and 4 in a dosing period were excluded.

The primary pharmacodynamic variable was the average daily urinary phosphate excretion over 3 days in each dosing period. The variable was assessed without transformation by using a mixed effect linear model with fixed effects for treatment sequence, dosing period and formulation, random effect for subject-within-sequence group, and period baseline as a covariate. The baseline measure was the average of total urinary phosphate excretion on Day −1 and Day 1 from each period. Based on the mixed effect linear model, a standard 90% confidence interval (CI) was constructed for the difference in least squares (LS) means of the primary pharmacodynamic variable between test Formulation A (capsule) and reference Formulation C (chewable tablet) and between test Formulation B (opened capsule) and reference Formulation C (chewable tablet). In addition, a reference interval representing ±120% of the LS mean (i.e. ±LS least squares means*20%) of the reference Formulation C was constructed. Pharmacodynamic equivalence was claimed if the 90% CI for the difference (A−C or B−C) was completely contained within the reference interval.

Subjects who provided non-quantifiable urine concentrations were included in the Pharmacodynamic Set by setting non-quantifiable values to 1.5; half the lower limit of detection of the assay.

The secondary pharmacodynamic variable was the urinary phosphate excretion on Day 4 (i.e., Day 3 to Day 4) and was assessed using the same model as for the primary variable.

Urinary phosphate excretion and change from baseline were summarized by formation using descriptive statistics (number of observations [n], mean, standard error [SE], coefficient of variation [CV %], median, minimum, and Maximum).

Statistical Methods: Pharmacokinetics

The pharmacokinetic population included subjects from the safety population with no major deviations related to intake of lanthanum carbonate, including all subjects in the safety population with sufficient post-dose blood samples taken to estimate $C_{max}$ and $AUC_{0-48}$ after dosing on day 4 in all treatment periods. Subjects who vomited between dosing and 10 hours post-dose on day 4 of a dosing period were excluded from the pharmacokinetic population.

The PK analysis included $C_{max}$, $t_{max}$, $AUC_{0-t}$, $AUC_{0-48}$, $\lambda_z$, and $t_{1/2}$, where $C_{max}$: Maximum plasma concentration $t_{max}$: Time to $C_{max}$ $AUC_{0-48}$: Area under the plasma concentration-time curve from time zero to 48 hours after dosing on Day 4

$AUC_{0-t}$: Area under the plasma concentration-time curve from time zero to time (t) of the last quantifiable plasma concentration (Ct)

$\lambda_z$: Apparent terminal phase rate constant $t_{1/2}$: Apparent terminal half-life.

Descriptive statistics (number of subjects, mean, standard deviation (SD), CV %, geometric mean, median, maximum, and minimum) were determined for the pharmacokinetic parameters of lanthanum. The pharmacokinetic parameters $C_{max}$, $AUC_{0-48}$ and $AUC_{0-t}$ of lanthanum were analyzed after logarithmic transformation using a standard mixed effect linear model. From the LS mean and SE of the difference (A−C), a 90% CI was constructed for the difference of the logs of A and B. To return to the original scale, an exponential transformation was applied to the lower and upper limits of the CI. This created a point estimate and 90% CI for the ratio of LS means for Formulation A to Formulation C In addition, $t_{max}$ was compared between formulations using the Wilcoxon signed rank test. The same models were used to compare Formulation B with Formulation C.

Results

Subject Disposition

Subject disposition is presented in Table 16.

TABLE 16

| Number of subjects (planned and analysed) | |
|---|---|
| | Overall |
| Enrolled subjects—n | 96 |
| Randomized subjects—n | 96 (100.0) |
| Safety set—n (%) | 96 (100.0) |
| Pharmacodynamic set—n (%) | 92 (95.8) |
| Pharmacokinetic set—n (%) | 91 (94.8) |
| Completed the study—n (%) | 91 (94.8) |
| Did not complete the study—n (%) | 5 (5.2) |

Pharmacodynamic Results

Table 17 presents the results of the pharmacodynamic analysis of the 3-day average of urinary phosphate excretion comparing capsules vs. chewable tablets and open capsules vs. chewable tablets. To conclude pharmacodynamic equivalence, the 90% CI must be contained within the Critical Reference Interval.

TABLE 17

The 3-day average of urinary phosphate excretion comparing capsules vs. chewable tablets and open capsules vs. chewable tablets.

| | Capsule (A) (N = 92) | Open Capsule (B) (N = 92) | Chewable Tablet (C) (N = 92) |
|---|---|---|---|
| Baseline | | | |
| Mean (SE) | 26.10 (0.617) | 26.22 (0.654) | 26.37 (0.714) |
| Min, Max | 14.3, 40.9 | 12.3, 41.4 | 10.0, 42.8 |
| Post-dose over 3 days | | | |
| Mean (SE) | 19.18 (0.626) | 15.34 (0.525) | 16.39 (0.615) |
| Min, Max | 6.9, 36.1 | 3.3, 25.9 | 2.6, 31.8 |

TABLE 17-continued

The 3-day average of urinary phosphate excretion comparing
capsules vs. chewable tablets and open capsules vs. chewable tablets.

|  | Capsule (A)<br>(N = 92) | Open Capsule (B)<br>(N = 92) | Chewable Tablet (C)<br>(N = 92) |
|---|---|---|---|
| LS Mean (SE) | 19.24 (0.427) | 15.35 (0.427) | 16.32 (0.427) |
| Difference of the LS Means | 2.92 | −0.97 | |
| 90% CI of the Difference | (2.21, 3.64) | (−1.68, −0.25) | |
| Critical Reference Interval* | | (−3.26, 3.26) | |

*±20% LSMean of reference Formulation C (chewable tablet)

Mean average urinary phosphate excretion reduced from a baseline of 26.10 mmol to 19.18 mmol for the capsule treatment and from a baseline of 26.37 mmol to 16.39 mmol for the chewable tablets treatment. The 90% CI of the difference was not entirely contained within the critical reference range and so pharmacodynamic equivalence between the lanthanum carbonate capsules and FOSRENOL® chewable tablets could not therefore be claimed.

In contrast, lanthanum carbonate opened capsules were shown to be pharmacodynamically equivalent to FOSRENOL® chewable tablets. Mean average urinary phosphate excretion reduced from a baseline of 26.22 mmol to 15.34 mmol for the opened capsules treatment and from a baseline of 26.37 mmol to 16.39 mmol for the chewable tablets treatment. The 90% CI of the difference was wholly contained within the critical reference interval.

Table 18 is a pharmacodynamic analysis of Day 4 urinary phosphate excretion comparing capsules vs. chewable tablets and open capsules vs. chewable tablets. In addition, a reference interval representing ±20% of the reference Formulation C LS mean was constructed,

TABLE 18

The Day 4 urinary phosphate excretion comparing capsules vs.
chewable tablets and open capsules vs. chewable tablets.

|  | Capsule (A)<br>(N = 92) | Open Capsule (B)<br>(N = 92) | Chewable Tablet (C)<br>(N = 92) |
|---|---|---|---|
| Baseline | | | |
| Mean (SE) | 26.10 (0.617) | 26.22 (0.654) | 26.37 (0.714) |
| Min, Max | 14.3, 40.9 | 12.3, 41.4 | 10.0, 42.8 |
| Post-dose at Day 4 | | | |
| Mean (SE) | 17.19 (0.666) | 13.77 (0.627) | 14.37 (0.721) |
| Min, Max | 6.2, 33.3 | 1.8, 29.2 | 2.5, 36.9 |
| LS Mean (SE) | 17.24 (0.563) | 13.78 (0.563) | 14.31 (0.563) |
| Difference of the LS Means | 2.93 | −0.53 | |
| 90% CI of the Difference | (1.90, 3.96) | (−1.56, 0.50) | |
| Critical Reference Interval* | | (−2.86, 2.86) | |

*±20% LSMean of reference Formulation C (chewable tablet)

Results for Day 4 urinary phosphate excretion were consistent with those for the 3-day average urinary phosphate excretion, with the 90% Confidence Interval of the difference was not entirely contained within the Critical Reference Interval for the capsule, but being wholly contained within this interval for the opened capsule.

Pharmacokinetic Results

Figure 11:
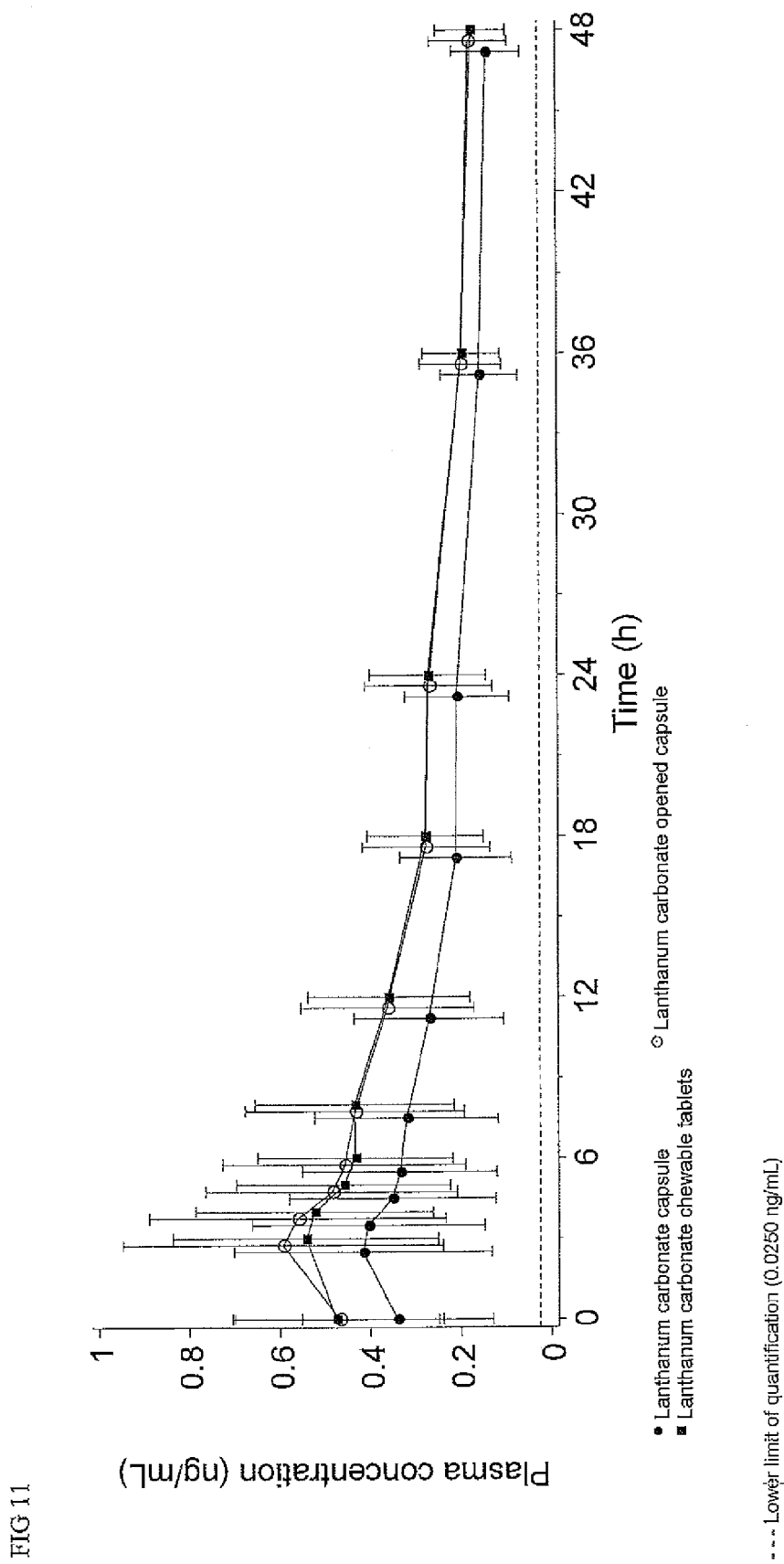
FIG. 11 is a graph showing the arithmetic mean (±SD) plasma concentration-time profiles of lanthanum following a final dose (1000 mg) of lanthanum carbonate as Regimen A (2×500 mg capsules), Regimen B (2×500 mg opened capsules), or Regimen C (2×500 mg chewable tablets)

FIG. 11 presents a graph displaying the mean plasma concentrations of lanthanum on Day 4 after oral administration of multiple tid doses of lanthanum carbonate as Regimen A (2×500 mg capsules), Regimen B (2×500 mg opened capsules), or Regimen C (2×500 mg chewable tablets). Table 19 is a summary of the PK parameters for these plasma concentrations of lanthanum. Table 20 is an analysis of the plasma lanthanum bioavailability parameters comparing the lanthanum carbonate capsules (Formulation A) and the lanthanum carbonate chewable tablets (Formulation C). Table 21 is an analysis of the plasma lanthanum bioavailability parameters comparing the lanthanum carbonate opened capsules (Formulation B) and the lanthanum carbonate chewable tablets (Formulation C).

TABLE 19

A summary of the PK parameters derived from the
plasma concentrations of lanthanum

|  | Capsule | Opened Capsule | Chewable Tablet |
|---|---|---|---|
| $AUC_{0-48}{}^{a}$ | 10.7 ± 6.13 | 14.2 ± 7.24 | 14.0 ± 6.44 |
| $C_{max}{}^{a}$ | 0.450 ± 0.288 | 1.609 ± 0.355 | 0.573 ± 0.292 |

TABLE 19-continued

A summary of the PK parameters derived from the
plasma concentrations of lanthanum

|  | Capsule | Opened Capsule | Chewable Tablet |
|---|---|---|---|
| $t_{max}{}^{b}$ | 3.00<br>(0.00-12.0) | 3.00<br>(0.00-8.00) | 3.00<br>(0.00-12.0) |

[a]Mean ± SD;
[b]Median (Range)

The $AUC_{0-t}$ was not reported because it was identical to $AUC_{0-48}$ (plasma lanthanum quantifiable in all subjects up to 48 hours after dosing of all formulations).

TABLE 20

Analysis of plasma lanthanum bioavailability parameters comparing Formulation A
(Lanthanum Carbonate Capsules) and C (Lanthanum Carbonate Chewable Tablets)

| Parameter | Geometric Least Squares Means | | Ratio of A:C | 90% CI for Ratio |
|---|---|---|---|---|
| | Lanthanum Carbonate Capsules (Formulation A) | Lanthanum Carbonate Chewable Tablets (Formulation C) | | |
| $AUC_{0-48}$ (ng.h/mL) | 9.37 | 12.6 | 0.742 | (0.703, 0784) |
| $C_{max}$ (ng/mL) | 0.387 | 0.509 | 0.761 | (0.711, 0.814) |
| $t_{max}^a$ | 3 | 3 | 0 | (0, 0.500) |

$^a$Median, median difference (90% CI for median difference)

The $AUC_{0-t}$ was not reported because it was identical to $AUC_{0-48}$ (plasma lanthanum quantifiable in all subjects up to 48 hours after dosing of all formulations).

TABLE 21

Analysis of plasma lanthanum bioavailability parameters comparing
Formulation B (Lanthanum Carbonate Opened Capsules) and C
(Lanthanum Carbonate Chewable Tablets)

| Parameter | Geometric Least Squares Means | | Ratio of B:C | 90% CI for Ratio |
|---|---|---|---|---|
| | Lanthanum Carbonate Opened Capsules (Formulation B) | Lanthanum Carbonate Chewable Tablets (Formulation C) | | |
| $AUC_{0-48}$ (ng·h/mL) | 12.7 | 12.6 | 1.00 | (0.950, 1.06) |
| $C_{max}$ (ng/mL) | 0.523 | 0.509 | 1.03 | (0.960, 1.10) |
| $t_{max}^a$ | 3 | 3 | 0 | (−0.500, 0) |

$^a$Median, median difference (90% CI for median difference)

The $AUC_{0-t}$ was not reported because it was identical to $AUC_{0-48}$ (plasma lanthanum quantifiable in all subjects up to 48 hours after dosing of all formulations).

Systemic exposure to lanthanum was, on average, approximately 25% lower for the capsule than for the chewable tablet, based on the mean ratio (A:C) for $AUC_{0-48}$ and $C_{max}$. However, on the same basis, the opened capsule was found to deliver similar lanthanum systemic exposure to that for the chewable tablet.

Safety Results

There were no deaths or other serious adverse events (SAEs). Two subjects discontinued the study due to AEs, 1 of which (allergic dermatitis) was treatment-emergent. The incidence of TEAEs was slightly higher after administration of lanthanum carbonate chewable tablets (13 subjects, 13.8%) as compared to the capsules (6 subjects, 6.5%) and opened capsules (8 subjects, 8.5%) formulations. The most common TEAEs were nausea and headache (both 7 subjects, 7.3% overall) and constipation (6 subjects, 6.3% overall).

Table 22 is a summary of the gastrointestinal (GI) treatment-emergent adverse events safety set.

TABLE 22

A summary of the GI treatment-emergent adverse events (Safety Set)

| System Organ Class Preferred Term | Formulation A (Capsule) (N = 93) | | Formulation B (Open Capsule) (N = 94) | | Formulation C (Chewable Tablet) (N = 94) | | Overall (n = 96) | |
|---|---|---|---|---|---|---|---|---|
| | Subjects n (%) | Events n | Subjects n (%) | Events n | Subjects n (%) | Events n | Subjects n (%) | Events n |
| Any Adverse Event | 6 (6.5) | 7 | 8 (8.5) | 9 | 13 (13.8) | 17 | 24 (25.0) | 33 |
| Gastrointestinal disorders | 4 (4.3) | 4 | 2 (2.1) | 2 | 8 (8.5) | 8 | 14 (14.6) | 14 |
| Constipation | 1 (1.1) | 1 | 2 (2.1) | 2 | 3 (3.2) | 3 | 6 (6.3) | 6 |
| Diarrhoea | 0 (0.0) | 0 | 0 (0.0) | 0 | 1 (1.1) | 1 | 1 (1.0) | 1 |
| Nausea | 3 (3.2) | 3 | 0 (0.0) | 0 | 4 (4.3) | 4 | 7 (7.3) | 7 |

Summary and Conclusions

Lanthanum carbonate capsules were found not to be pharmacodynamically equivalent to lanthanum carbonate chewable tablets. However, lanthanum carbonate opened capsules were found to be pharmacodynamically equivalent to lanthanum carbonate chewable tablets.

Based on the statistical analysis of $AUC_{0-48}$ and $C_{max}$, plasma lanthanum concentrations were approximately 25% lower for the capsule than for the chewable tablet while plasma lanthanum concentrations were similar for the opened capsule and for the chewable tablet. The rate of absorption of lanthanum was also lower from the capsules than from the chewable tablet formulation, based on achievement of a lower value for the capsules at the same median $t_{max}$ as that for the chewable tablet. Overall, lanthanum carbonate capsules (intact and opened) and lanthanum carbonate chewable tablets were well tolerated. There was no clinically relevant difference between the groups in any of the safety parameters assessed.

Example 14

A Phase 1 Pharmacodynamic Equivalence Study Comparing Urinary Phosphate Excretion and Plasma Lanthanum Pharmacokinetics for a Lanthanum Carbonate Granule* Formulation and Lanthanum Carbonate Chewable Tablets Administered to Healthy Adult Subjects *subsequently known as oral powder Objectives: Primary To compare the average daily urinary phosphate excretion over 3 days following dosing between a lanthanum carbonate granules formulation (formulation A) and lanthanum carbonate chewable tablets (formulation B), administered as 1000 mg 3 times per day with apple-sauce, immediately following meals.

Objectives: Secondary (1) To compare urinary phosphate excretion on Day 4 following 3 days of dosing with a lanthanum carbonate granules formulation (formulation A) and lanthanum carbonate chewable tablets (formulation B)

(2) To assess the safety and tolerability of a lanthanum carbonate granules formulation (formulation A) with lanthanum carbonate chewable tablets (formulation B)

(3) To compare the lanthanum pharmacokinetic profiles of a lanthanum carbonate granules formulation (formulation A) with lanthanum carbonate chewable tablets (formulation B).

Study Design

This was a randomized, open-label, 2-period, cross-over study in healthy male and female volunteers (aged 18-55 years at the time of consent) conducted at a single study center. There was a screening period followed by 2 dosing periods for each subject. Subjects were dosed with either granules formulation A or the reference chewable tablet formulation B according to their randomization during each study period. There was a washout period of at least 14 days between dosing periods.

For formulation A (containing 68.14 wt % lanthanum carbonate tetrahydrate, 30.56 wt % dextrates (hydrated), 1.0 wt % colloidal silicon dioxide, and 0.3 wt % magnesium stearate, batch number: 807012), subjects received 1 lanthanum carbonate granules sachet (1000 mg/dose) after meals 3 times daily for 3 days followed by a single granules sachet (1000 mg) on Day 4, administered immediately following breakfast. Each dose was administered sprinkled on 1 tablespoon of apple sauce.

For formulation B (lanthanum carbonate available as Fosrenol® from Shire, Wayne, Pa. containing the same percentages of ingredients as Formulation C of Example 13, batch number: A38683B), subjects received 1 chewable tablet of FOSRENOL® (1×1000 mg/tablet) after meals, 3 times daily for 3 days followed by a single dose on Day 4 immediately following breakfast. Subjects received 1 chewable tablet and then immediately ingested 1 tablespoon of apple sauce after taking the tablet.

Sufficient subjects were randomized to ensure a minimum of 46 subjects completed the study.

Criteria for Evaluation

Urine was collected over 24 hour periods as: Day −2 to Day −1; Day −1 to Day 1; Day 1 to Day 2; Day 2 to Day 3 and Day 3 to Day 4. Each collection started with 30 minutes before the morning meal and ended 24 hours later. Urinary phosphate excretion analysis was the primary evaluation for the determination of pharmacodynamic equivalence for this study.

As a secondary evaluation, pharmacokinetic assessments were performed by inductively coupled plasma mass spectrometry following determination of plasma concentrations of lanthanum at the following times: pre-dose (within 30 minutes prior to the start of the morning meal) on Days 1, 2, 3 and 4 and at 3, 4, 5, 6, 8, 12, 18, 24, 36 and 48 hours after the final morning dose on Day 4.

Statistical Methods: Pharmacodynamics

Subjects included in the safety population took at least one dose of lanthanum carbonate and had at least one post-dose safety assessment. The pharmacodynamic population included all evaluable subjects from the safety population with no major protocol deviations, including all subjects in the safety population who completed all urine collections and consumed at least 95% of food in all treatment periods. Subjects who vomited between days −2 and 4 in a dosing period were excluded.

The primary pharmacodynamic variable was the average daily urinary phosphate excretion over 3 days in each dosing period. The variable was assessed without transformation by using a mixed effect linear model with fixed effects for treatment sequence, dosing period and formulation, random effect for subject-within-sequence group, and period baseline as a covariate. The baseline measure was the average of total urinary phosphate excretion on Day −1 and Day 1 from each period. Based on the mixed effect linear model, a standard 90% confidence interval (CI) was constructed for the difference in least squares (LS) means of the primary pharmacodynamic variable between test formulation A (granules) and reference formulation B (chewable tablet). In addition, a reference interval representing ±20% of the reference formulation. B LS mean (i.e. LS least squares means*20%) was constructed. Pharmacodynamic equivalence was claimed if the 90% CI for the difference (A−B) was completely contained within the reference interval.

Subjects who provided non-quantifiable urine concentrations were included in the Pharmacodynamic Set by setting non-quantifiable values to 1.5; half the lower limit of detection of the assay.

The secondary pharmacodynamic variable was assessed by using a mixed effect linear model with fixed effects for sequence group, period and formulations, random effect for subject within sequence group, and period baseline as a covariate. Based on the mixed effect linear model, a standard 90% CI was constructed for the difference in LS means of the secondary pharmacodynamic variable between test formulation A and reference formulation B. In addition, a reference interval representing ±20% of the reference formulation B LS mean was constructed.

Urinary phosphate excretion and change from baseline were summarized by formulation using descriptive statistics (number of observations [n], mean, standard error [SE], coefficient of variation [CV %], median, minimum, and maximum).

Statistical Methods: Pharmacokinetics

The pharmacokinetic population included subjects from the safety population with no major deviations related to intake of lanthanum carbonate, including all subjects in the safety population with sufficient post-dose blood samples taken to estimate $C_{max}$ and $AUC_{0-48}$ after dosing on day 4 in all treatment periods. Subjects who vomited between dosing and 10 hours post-dose on day 4 of a dosing period were excluded from the pharmacokinetic population.

The PK analysis included $C_{max}$, $t_{max}$, $AUC_{0-t}$, $AUC_{0-48}$, $\lambda_z$, and $t_{1/2}$, where the means of these terms are the same as in Example 13. Descriptive statistics (number of subjects, mean, standard deviation (SD), CV %, geometric mean, median, maximum, and minimum) were determined for the pharmacokinetic parameters of lanthanum. The pharmacokinetic parameters $C_{max}$, $AUC_{0-48}$ and $AUC_{0-t}$ of lanthanum were analyzed after logarithmic transformation using a standard mixed effect linear model. From the LS mean and SE of the difference (A–B), a 90% CI was constructed for the difference of the logs of A and B. To return to the original scale, an exponential transformation was applied to the lower and upper limits of the CI. This created a point estimate and 90% CI for the ratio of LS means for Formulation A to Formulation B. In addition, $t_{max}$ was compared between formulations using the Wilcoxon signed rank test.

Results

Subject Disposition

Subject disposition is presented in Table 23.

TABLE 23

Number of subjects (planned and analyzed)

| | Overall (N = 72) |
|---|---|
| Enrolled subjects - n | 72 |
| Randomized subjects - n | 72 |
| Safety set - n (%) | 72 (100.0) |
| Pharmacodynamic set - n (%) | 53 (73.6) |
| Pharmacokinetic set - n (%) | 64 (88.9) |
| Completed the study - n (%) | 56 (77.8) |
| Did not complete the study - n (%) | 16 (22.2) |

Pharmacodynamic Results

Table 24 presents the results of the pharmacodynamic analysis of the 3-day average of urinary phosphate excretion comparing granules and chewable tablets.

TABLE 24

Analysis of 3-Day Average of Urinary Phosphate Excretion

| | A (Granules) N = 53 | B (Chewable Tablet) N = 53 |
|---|---|---|
| Average Daily Urinary Phosphate Excretion (mmol) Baseline | | |
| Mean (SE) | 30.63 (0.865) | 29.43 (0.876) |
| Min, Max | 14.99, 43.95 | 18.27, 42.79 |
| Post-dose over 3 Days | | |
| Mean (SE) | 15.28 (0.565) | 16.57 (0.602) |
| Coefficient of Variation (%) | 26.937 | 26.468 |
| Median | 15.15 | 16.25 |
| Min, Max | 3.76, 23.22 | 7.81, 25.05 |
| LS Mean (SE) | 15.16 (0.477) | 16.76 (0.476) |
| Difference of the LS Means[b] | −1.60 | |
| 90% CI of the Difference | (−2.38, −0.82) | |
| Critical Reference Interval * | (−3.35, 3.35) | |

* ±20% of the reference formulation B LS mean.

The primary analysis of 3 day average urinary phosphate excretion demonstrated lanthanum carbonate granules to be pharmacodynamically equivalent to FOSRENOL® chewable tablets. Mean average urinary phosphate excretion reduced from a baseline of 30.63 mmol to 15.28 mmol for the granules treatment and from a baseline of 29.43 mmol to 16.57 mmol for the chewable tablets treatment. The 90% CI of the difference was entirely contained within the critical reference interval.

Table 25 is a pharmacodynamic analysis of Day 4 urinary phosphate excretion comparing granules and chewable tablets.

TABLE 25

Analysis of Day 4 Urinary Phosphate Excretion

| | A (Granules) N = 53 | B (Chewable Tablet) N = 53 |
|---|---|---|
| Day 4 Urinary Phosphate Excretion (mmol) Baseline | | |
| Mean (SE) | 30.63 (0.865) | 29.43 (0.876) |
| Min, Max | 14.99, 43.95 | 18.27, 42.79 |
| Day 4 | | |
| Mean (SE) | 14.49 (0.644) | 15.86 (0.712) |
| Min, Max | 3.78, 23.91 | 3.21 30.61 |
| LS Mean (SE) | 14.39 (0.617) | 16.05 (0.616) |
| Difference of the LS Means | −1.66 | |
| 90% CI of the Difference | (−2.85, −0.48) | |
| Critical Reference* | (−3.21, 3.21) | |

*±20% of the reference formulation B LS mean.

The secondary analysis of urinary phosphate excretion on Day 4 supported the finding of the primary analysis. Mean average urinary phosphate excretion reduced from a baseline of 30.63 mmol to 14.49 mmol for the granules treatment and from a baseline of 29.43 mmol to 15.86 mmol for the chewable tablets treatment. Again, the 90% CI of the difference was entirely contained within the critical reference interval.

Pharmacokinetic Results

Figure 12:
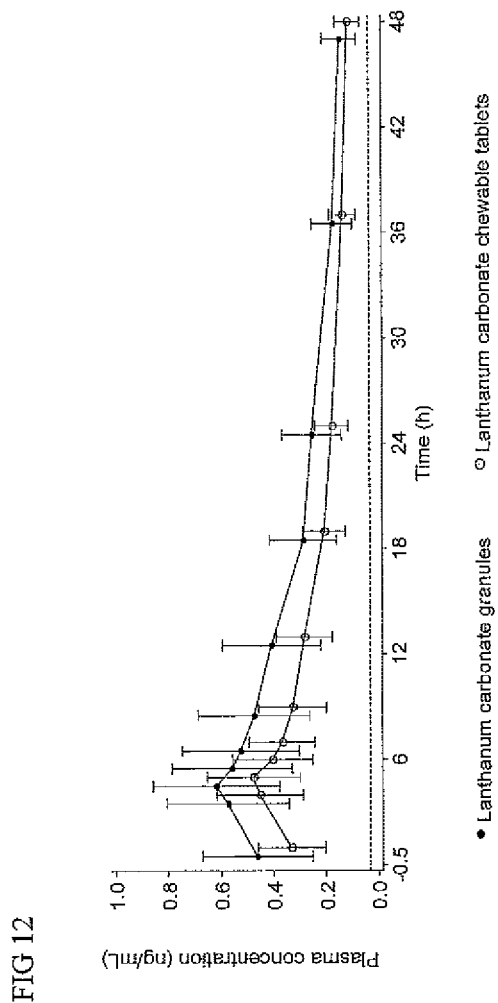
FIG. 12 is a graph showing the arithmetic mean (±SD) concentration-time profiles for plasma lanthanum for all subjects in the pharmacokinetic set following a final dose (1000 mg) of lanthanum carbonate as Regimen A (1000 mg granules) or Regimen B (1000 mg chewable tablets).

FIG. 12 presents a graph displaying the mean plasma concentrations of lanthanum on Day 4 after oral administration of multiple lid doses of lanthanum carbonate as Regimen A (1000 mg granules) or Regimen B (1000 mg chewable tablets). Table 26 is a summary of the PK parameters for these plasma concentrations of lanthanum. Table 27 is an analysis of the plasma lanthanum bioavailability parameters comparing the lanthanum carbonate granules (Formulation A) and the lanthanum carbonate chewable tablets (Formulation B).

The pharmacokinetic parameters of lanthanum and associated statistical analysis, following administration of the final dose of lanthanum carbonate granules and lanthanum carbonate chewable tablets, are presented in Tables 26 and 27, respectively.

TABLE 26

The pharmacokinetic parameters of lanthanum in plasma following administration of the final dose of lanthanum carbonate granules and lanthanum carbonate chewable tablets

| Parameter | Lanthanum carbonate granules (Formulation A) (N = 64) | Lanthanum carbonate chewable tablets (Formulation B) (N = 58) |
|---|---|---|
| $AUC_{0-48}$ (ng·h/mL) | 14.2[b] (6.02) | 10.3 (3.50) |
| $C_{max}$ (ng/mL) | 0.638 (0.241) | 0.504 (0.181) |
| $t_{max}$[a] (h) | 4.00 (0-6.00) | 4.00 (0-8.00) |
| $t_{1/2}$ (h) | 21.9[c] (2.96) | 22.3[d] (3.37) |

Arithmetic mean (SD) data are presented

N = Number of subjects

[a]Median (min-max)

[b]N = 62,

[c]N = 28

[d]N = 23

TABLE 27

The pharmacokinetic parameters and statistical analysis of lanthanum in plasma following administration of the final dose of lanthanum carbonate granules and lanthanum carbonate chewable tablets

| | Geometric least squares (LS) means | | |
|---|---|---|---|
| Parameter | Lanthanum carbonate granules (Formulation A) | Lanthanum carbonate chewable tablets (Formulation B) | Ratio of geometric LS means (90% CI) (A:B) |
| $AUC_{0-48}$ (ng·h/mL) | 13.11 | 9.80 | 1.34 (1.26, 1.42) |
| $AUC_{0-t}$ (ng·h/mL) | 13.11 | 9.80 | 1.34 (1.26, 1.42) |
| $C_{max}$ (ng/mL) | 0.60 | 0.47 | 1.26 (1.20, 1.33) |
| $t_{max}$[a] (h) | 4 | 4 | 0.01 (0.00, 0.50) |

[a]Median, Median difference (90% CI) (A-B) on untransformed data.

Systemic exposure to lanthanum was higher for the granules than for the chewable tablet, approximately 30% based on the ratios (A:B) for $AUC_{0-48}$ and $C_{max}$, and was more variable.

Safety Results

There were no deaths or other serious adverse events (SAES). One subject developed treatment-emergent adverse events (TEAEs) leading to discontinuation (abdominal distension and vomiting). The adverse events were judged by the investigator to be unrelated to study medication.

The incidence of TEAEs was higher after the administration of the granules formulation (23 subjects, 32.4%) than after chewable tablets (14 subjects, 23.0%). The difference between the groups with regard to the incidence of TEAEs was largely attributable to gastrointestinal disorders (13 subjects, 18.3% granules formulation and 4 subjects, 6.6% chewable tablets), which comprised the system organ class most commonly associated with TEAEs. Table 28 is a summary of the gastrointestinal (GI) treatment-emergent adverse events safety set.

TABLE 28

Summary of TEAEs in the Gastrointestinal System Organ Class

| | A (Granules) N = 71 | | B (Chewable Tablet) N = 61 | | Overall N = 72 | |
|---|---|---|---|---|---|---|
| | n (%) | events | n (%) | events | n (%) | events |
| Gastrointestinal disorders | 13 (18.3) | 19 | 4 (6.6) | 5 | 15 (20.8) | 24 |
| Nausea | 6 (8.5) | 7 | 3 (4.9) | 3 | 8 (11.1) | 10 |
| Abdominal pain upper | 3 (4.2) | 3 | 1 (1.6) | 1 | 3 (4.2) | 4 |
| Dyspepsia | 2 (2.8) | 2 | 0 | 0 | 2 (2.8) | 2 |
| Abdominal discomfort | 1 (1.4) | 1 | 0 | 0 | 1 (1.4) | 1 |
| Abdominal distension | 1 (1.4) | 1 | 0 | 0 | 1 (1.4) | 1 |
| Abdominal pain | 1 (1.4) | 1 | 0 | 0 | 1 (1.4) | 1 |
| Constipation | 1 (1.4) | 1 | 0 | 0 | 1 (1.4) | 1 |
| Diarrhea | 1 (1.4) | 1 | 0 | 0 | 1 (1.4) | 1 |
| Dry mouth | 0 | 0 | 1 (1.6) | 1 | 1 (1.4) | 1 |
| Epigastric discomfort | 1 (1.4) | 1 | 0 | 0 | 1 (1.4) | 1 |
| Vomiting | 1 (1.4) | 1 | 0 | 0 | 1 (1.4) | 1 |

Note:
AEs were coded using the MedDRA 12.0 AE dictionary.

Note:
Percentages are based on the number of subjects in the Safety Set.

Note:
AEs were considered treatment-emergent if they occurred at or after the first dose of study medication; or were present prior to the first dose but worsened in severity; and up to and including Day 6 or discharge day for each period.

The most common TEAEs were nausea (6 subjects, 8.5% granules formulation and 3 subjects, 4.9% chewable tablets) and headache (4 subjects, 5.6% granules formulation and 3 subjects, 4.9% chewable tablets). There was a slightly higher incidence of TEAEs judged by the investigator to be treatment-related in the granules group (14 subjects, 19.7%) as compared to the chewable tablets (8 subjects, 13.1%). Most TEAEs were mild and transient, and no subjects experienced a severe TEAE.

There were no clinically relevant findings in the clinical laboratory tests, physical examination, vital signs or 12-lead ECG results.

Summary and Conclusions

Lanthanum carbonate granules were found to be pharmacodynamically equivalent to FOSRENOL® chewable tablets.

The systemic exposure to lanthanum (based on $AUC_{0-48}$ and $C_{max}$) was approximately 30% higher and more variable following administration of lanthanum carbonate granules than following administration of lanthanum carbonate chewable tablets. The rate of absorption of lanthanum was also greater from the granules formulation than from the chewable tablet, based on achievement of a higher $C_{max}$ value for the granules at the same median $t_{max}$ as that for the tablet.

Based on what is known regarding the pharmacokinetic variability, toxicity, accumulation and excretion of lanthanum, this approximately 30% increase in $AUC_{0-48}$ and $C_{max}$ following granules administration is not expected to have any clinical relevance or to alter the overall risk profile of lanthanum carbonate granules formulation compared to the chewable tablet.

Overall, both lanthanum carbonate formulations were well-tolerated. The modest differences between the treatment groups with regard to the incidence of gastrointestinal events was well within the variation seen in the FOSRENOL Phase 1 program and is unlikely to be of clinical relevance.

Example 15

The Manufacture of Stick Packs Containing 500 Mg or 1000 Mg Elemental Lanthanum as Lanthanum Carbonate in a Powder This Example demonstrates the fill ability of capsule contents to be filled into stick packs instead of capsules. The powder capsule contents were packaged at two filling weights corresponding to 500 mg and 1000 mg elemental lanthanum as lanthanum carbonate.

Manufacturing of Final Granules

The manufacturing process for the powder was performed at a batch size of 110 kg. Table 29 shows the formulation and the batch numbers of ingredients:

TABLE 29

Powder formulation ingredients

| Ingredient | Batch | Amount (kg) | % (wt/wt) |
|---|---|---|---|
| Lanthanum carbonate | 3011914 | 95.400 | 86.7 |
| Dextrates | 3301606 | 9.0725 | 8.2 |
| Colloidal silicon dioxide | 3314396 | 1.100 | 1.0 |
| Crospovidone | 2607320 | 4.400 | 4.0 |
| Talc | 2248128 | 0.0275 | 0.025 |

The ingredients were weighed and sieved with a 1 mm hand sieve. Lanthanum carbonate, dextrates and crospovidone were blended for 40 min on a tumble blender (available from Servolift®, Wharton, N.J.) at 6 rpm. Afterwards, colloidal silicon dioxide and talc were added and blended for a further 5 minutes at 6 rpm. The final blend was compacted on a roller compactor and granules broken with a 1.25 mm sieve. Powder was blended on a Servolift® tumble blender for 5 minutes at 6 rpm.

The process parameters are listed in Table 30:

TABLE 30

Process parameters of final powders

| Manufacturing step | parameter | result |
|---|---|---|
| Pre-blend | Rotation speed [rpm] | 6 |
|  | Time [min] | 40 |
| Final blend | Rotation speed [rpm] | 6 |
|  | Time [min] | 5 |
| Roller compaction | Screw rotation [rpm] | 67 |
|  | Screw size | 3 |
|  | Roller rotation [rpm] | 11.0 |
|  | Compression force [kN] | 35 |
|  | Roller type | corrugated |
|  | Sieve rotation [rpm] | 75 |
|  | Sieve size [mm] | 1.25 |
|  | Temperature [° C.] | 18.3-21.5 |

A sample of powder was taken for measurement of particle size distribution and density. The results are listed in Table 31:

TABLE 31

Physical characteristics of final blend

| | method | results | |
|---|---|---|---|
| Bulk density | Ph.Eur. 2.9.15 | 1.087 g/ml | |
| Tapped density | Ph.Eur. 2.9.15 | 1.370 g/ml | |
| Particle size distribution | Ph.Eur. 2.9.12 | <63 μm | 29.3% |
| | | 63-90 μm | 12.7% |
| | | 90-125 μm | 9.0% |

TABLE 31-continued

Physical characteristics of final blend

| method | results | |
|---|---|---|
| | 125-250 μm | 17.7% |
| | 250-500 μm | 16.6% |
| | 500-710 μm | 9.9% |
| | 710-1000 μm | 4.5% |
| | >1000 μm | 0.3% |
| D10 | <90 μm | 42.0% |
| D50 | <500 μm | 85.3% |
| D90 | <1000 μm | 99.7% |

Stick Pack Filling Trials

The powders were filled into stick packs with two filling weights corresponding to 500 mg and 1000 mg lanthanum as lanthanum carbonate. 10,000 stick packs per dosage strength were filled as shown in Table 32.

TABLE 32

Stick pack filling

| strength | filling weight | stick pack size |
|---|---|---|
| 500 mg | 1,100 mg | 70 × 23 mm |
| 1000 mg | 2,200 mg | 70 × 23 mm |

For stick pack filling, unprinted laminate foil was used.

The packaging process was performed on stick pack line Merz SB51-1 (available from Merz, Lich, Germany) by using the set up parameters listed in Table 33:

TABLE 33

Packaging parameter for stick packs

| Parameter | result |
|---|---|
| Dosing auger [mm] | 8 |
| Heating length sealing [° C.] | 115-120 |
| Heating width sealing [° C.] | 205-210 |
| Heating FIN side [° C.] | 105-115 |
| Sealing pressure [bar] | 7.9-8.5 |
| Auger speed [%] | 60-70 |
| Line speed [sticks/min] | 40-60 |
| Check weighing balance [%] | ±5 |

During packaging 100% check weighing and in process testing was performed to monitor the stick pack filling process. The results of the in process control testing are listed in Tables 34 and 35.

TABLE 34

In-process control results for the 1000 mg dosage strength

| Test parameter | Result 1 hour | Result 2 hours | Result 3 hours |
|---|---|---|---|
| Appearance of bulk | Comply | Comply | Comply |
| Sealing image | Comply | Comply | Comply |
| Tightness vacuum test | Comply | Comply | Comply |
| Relative humidity (room) [%] | 16 | 16 | 16 |
| Room temperature [° C.] | 21 | 21 | 20 |
| Mean weight [mg] | 2178.4 | 2164.8 | 2174.4 |
| Weight variation (RSD) [%] | 1.1 | 0.9 | 1.0 |
| Waste (check weighing) [%] | | 2 | |

TABLE 35

In-process control results for the 500 mg dosage strength

| Test parameter | Result 1 hour | Result 2 hours | Result 3 hours | Result 4 hours | Result 5 hours |
|---|---|---|---|---|---|
| Appearance of bulk | Comply | Comply | Comply | Comply | Comply |
| Sealing image | Comply | Comply | Comply | Comply | Comply |
| Tightness vacuum test | Comply | Comply | Comply | Comply | Comply |
| Rel. humidity (room) [%] | 15 | 15 | 16 | 16 | 16 |
| Room temperature [° C.] | 21 | 21 | 21 | 21 | 21 |
| Mean weight [mg] | 1,094.3 | 1,090.4 | 1,092.7 | 1,085.5 | 1,055.6 |
| Weight variation (RSD) [%] | 2.3 | 1.5 | 2.7 | 1.7 | 2.2 |
| Waste (check weighing) [%] | | | 7 | | |

Stick pack filling process runs were very consistent without any issues. Waste and weight variations were higher during the packaging of the 500 mg dosage strength caused by the lower fill weight of 1,100 mg. For batch sizes larger than 10,000 stick packs the percentage of waste, which is produced mainly during set up of the packaging line, will be significantly lower. The fill weight of 2,200 mg for the 1000 mg dosage strength showed no filling or sealing issues so the stick pack size of 70×23 mm can be considered acceptable for both dosage strengths.

Analytical Testing of Final Stick Packs

Final testing on stick packs was performed according to the tests and specifications listed in Table 36. The analytical results are listed in Tables 36 and 37. All results comply with the current specification.

TABLE 36

Analytical testing for the 1000 mg stick packs

| Test: | Specification | Batch 3341481 |
|---|---|---|
| Appearance of bulk | white to off-white granules | complies |
| Mean Weight | 2,200 mg ± 5% (2,090-2,310 mg) | 2,190.40 mg (RED 2.1%) |
| Uniformity of Dosage Units | complies Ph.Eur 2.9.40 n = 10 | 98.78% AV 2.92 |
| Lanthanum Assay | 92.5-107.5% of label claim (1000 mg lanthanum) | 99.03% (98.9-99.1%) |
| Moisture (Karl Fischer) | for information only | 1.13% |
| Dissolution Lanthanum | complies Ph.Eur. 2.9.3 apparatus 2, 50 rpm, 0.25 mol/L HCl Q 80% after 30 minutes dissolution | 98.8% (97.5-100.3%) |

TABLE 37

Analytical testing for the 500 mg stick packs

| Test: | Specification | Batch 3341473 |
|---|---|---|
| Appearance | white to off-white granules | complies |
| Mean Weight | 1,100 mg ± 5% (1,045-1,155 mg) | 1,084.37 (RSD 2.7%) |
| Uniformity of Dosage Units | complies Ph.Eur. 2.9.40 n = 10 AV < 15.0 | 99.39% AV 2.24 |
| Lanthanum Assay | 92.5-107.5% of label claim (500 mg Lanthanum) | 99.15% (99.1-99.2%) |
| Moisture (Karl Fischer) | for information only | 1.15% |
| Dissolution Lanthanum | complies Ph.Eur. 2.9.3 apparatus 2, 50 rpm; 0.25 mol/L HCl Q 80% after 30 minutes dissolution | 97.9% (96.0-99.2%) |

Summary

The stick pack filling of the lanthanum carbonate powder formulation was successful. A stick pack size of 70×23 mm is acceptable for filling powder in a range of 1,100-2,200 mg corresponding to 500 mg-1000 mg elemental lanthanum as lanthanum carbonate.

The present invention is not to be limited in scope by the specific embodiments described herein. Indeed, various modifications of the invention in addition to those described herein will be apparent to those skilled in the art from the foregoing description. Such modifications are intended to fall within the scope of the appended claims.

All references cited herein, including all patents, published patent applications, and published scientific articles and books, are incorporated by reference in their entireties for all purposes.

The invention claimed is:

1. An oral pharmaceutical powder comprising:
   (1) lanthanum carbonate or lanthanum carbonate hydrate in an amount of 68.14% by weight;
   (2) dextrates in an amount of 30.56% by weight;
   (3) colloidal silicon dioxide in an amount of 1.0% by weight; and
   (4) magnesium stearate in an amount of 0.3% by weight.

2. The oral pharmaceutical powder of claim 1, wherein the powder is in an amount of about 750 mg or about 1000 mg elemental lanthanum.

3. The oral pharmaceutical powder of claim 1, wherein the powder is filled into one or more sachets, stick packs, or rigid containers.

* * * * *